US008859198B2

(12) United States Patent
Bartholomeusz et al.

(10) Patent No.: US 8,859,198 B2
(45) Date of Patent: Oct. 14, 2014

(54) DETECTION AND USE OF ANTIVIRAL RESISTANCE MUTATIONS

(75) Inventors: Angeline Ingrid Bartholomeusz, Carnegie (AU); Stephen Locarnini, Balaclava (AU); Anna Ayre, Brunswick West (AU); Lilly Ka Wai Yuen, Bulleen (AU); Peter William Angus, East Ivanhoe (AU); Joseph John Sasadeusz, Camberell (AU); Paul Desmond, Albert Park (AU); Hans Tillman, Leipzig (DE); Thomas Bock, Tuebingen (DE); William Sievert, Canterbury (AU); Sharon Lewin, Armadale (AU)

(73) Assignee: ABL SA, Luxembourg (LU)

( * ) Notice: Subject to any disclaimer, the term of this patent is extended or adjusted under 35 U.S.C. 154(b) by 807 days.

(21) Appl. No.: 12/303,942

(22) PCT Filed: Jun. 4, 2007

(86) PCT No.: PCT/AU2007/000785
§ 371 (c)(1),
(2), (4) Date: May 4, 2009

(87) PCT Pub. No.: WO2007/140522
PCT Pub. Date: Dec. 13, 2007

(65) Prior Publication Data
US 2010/0075299 A1    Mar. 25, 2010

(30) Foreign Application Priority Data

Jun. 6, 2006 (AU) .............................. 2006903065

(51) Int. Cl.
*C12Q 1/70* (2006.01)
*A61K 39/00* (2006.01)
*A61K 39/29* (2006.01)
*A61K 39/25* (2006.01)
*C12N 7/00* (2006.01)
*C07K 14/005* (2006.01)

(52) U.S. Cl.
CPC ........ *C12N 7/00* (2013.01); *C12N 2730/10134* (2013.01); *A61K 39/29* (2013.01); *C12N 2730/10122* (2013.01); *C07K 14/005* (2013.01)
USPC ....... 435/5; 424/184.1; 424/185.1; 424/189.1

(58) Field of Classification Search
None
See application file for complete search history.

(56) References Cited

U.S. PATENT DOCUMENTS

| 7,384,747 | B2 | 6/2008 | Bartholomeusz et al. | |
|---|---|---|---|---|
| 2004/0194155 | A1 | 9/2004 | Delaney et al. | |
| 2006/0051743 | A1* | 3/2006 | Bartholomeusz et al. | 435/5 |
| 2006/0190186 | A1 | 8/2006 | Bartholomeusz et al. | |

FOREIGN PATENT DOCUMENTS

| CA | 2309379 A1 | 12/2001 |
|---|---|---|
| WO | WO 03/080824 A1 | 10/2003 |
| WO | WO 03/087351 A1 | 10/2003 |
| WO | WO 2005/042733 A1 | 5/2005 |
| WO | WO 2006/034545 A1 | 4/2006 |
| WO | WO 2006/097284 A1 | 9/2006 |
| WO | WO 2006/105597 A1 | 10/2006 |
| WO | WO 2007/045045 A1 | 4/2007 |

OTHER PUBLICATIONS

Stuyver et al., Nomenclature for Antiviral-Resistant Human Hepatitis B Virus Mutations in the Polymerase Region, 2001, Hepatology, vol. 33, pp. 751-757.*
Saiki et al., Genetic analysis of amplified DNA with immobilized sequence-specific oligonucleotide probes, 1989, PNAS, vol. 86, pp. 6230-6234.*
Brunelle, M-N., et al. 2005 "Susceptibility to Antivirals of a Human HBV Strain with Mutations Conferring Resistance to Both Lamivudine and Adefovir" *Hepatology* 41:1391-1398.
Tenney, D.J., et al. 2004"Clinical Emergence of Entecavir-Resistant Hepatitis B Virus Requires Additional Substitutions in Virus Already Resistant to Lamivudine" *Antimicrobial Agents and Chemotherapy* 48: 3498-3507.
Torresi, J., et al. 2002 "Restoration of Replication Phenotype of Lamivudine-Resistant Hepatitis B Virus Mutants by Compensatory Changes in the 'Fingers' Subdomain of the Viral Polymerase Selected as a Consequence of Mutations in the Overlapping S Gene" *Virology* 299:88-99.
Walters, K-A., et al. 2003 "Generation of Stable Cell Lines Expressing Lamivudine-Resistant Hepatitis B Virus for Antiviral-Compound Screenin", *Antimicrobial Agents and Chemotherapy* 47: 1936-1942.
Angus, P. et al. 2003 "Resistance to adefovir dipivoxil therapy associated with the selection of a novel mutation in the HBV polymerase" *Gastroenterology* 125(2): 292-297.
Germer, J.J. et al. 2003 "Characterization of hepatitis B virus surface antigen and polymerase mutations in liver transplant recipients pre- and post-transplant" *Am. J. of Transplantation* 3:743-753.
Jolivet-Reynaud, C. et al. 2001 "Localization of hepatitis B surface antigen epitopes present on variants and specifically recognized by anti-hepatitis B surface antigen monoclonal antibodies". *J. of Med. Virol.* 65:241-249.
Locarnini, S. 2004 "Molecular virology of hepatitis B virus". *Seminars in Liver Disease* 24(1):3-10.

(Continued)

*Primary Examiner* — Benjamin P Blumel
(74) *Attorney, Agent, or Firm* — Hultquist, PLLC

(57) ABSTRACT

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. Vaccines and diagnostic assays are also contemplated herein.

7 Claims, 14 Drawing Sheets

(56) References Cited

OTHER PUBLICATIONS

Sablon, E & Shapiro, F. 2005 "Advances in molecular diagnosis of HBV infection and drug resistance". *Int. J. of Medical Sciences* 2(1):8-16.

Tacke, F et al. 2004 "Influence of mutations in the Hepatitis B Virus genome on virus replication and drug resistance—Implications for novel antiviral strategies" *Current Medicinal Chemistry* 11:2667-2677.

Torresi, J. et al. 2002 "The virological and clinical significance of mutations in the overlapping envelope and polymerase genes of hepatitis B virus", *J. of Clin. Virol.* 25(2):97-106.

* cited by examiner

Patient A
TCCACCTCTAAGAGACAGTCATCCTCAGGCCATGCAGTGGAATTCCACTGCC
TTCCACCAAGCTCTGCAGGATCCCAGAGTCAGGGGTCTGTATTTTCCTGCTG
GTGGCTCCAGTTCAGGAACAGTAAACCCTGCTCCGAATATTGCCTCTCACAT
CTCGTCAATCTCCGCGAGGACTGGGGACCCTGTGACGAACATGGAGAACAT
CACATCAGGATTCCTAGGACCCCTGCTCGTGTTACAGGCGGGGTTTTTCTTG
TTGACAAGAATCCTCACAATACCGCAGAGTCTAGACTCGTGGTGGACTTCTCT
CAATTTTCTAGGGGGATCACCCGTGTGTCTTGGCCAAAATTCGCAGTCCCCA
ACCTCCAATCACTCACCAACCTCCTGTCCTCCAATTTGTCCTGGTTATCGCTG
GATGTGTCTGCGGCGTTTTATCATATTCCTCTTCATCCTGCTGCTATGCCTCA
TCTTCTTATTGGTTCTTCTGGATTATCAAGGTATGTTGCCCGTTTGTCCTCTAA
TTCCAGGATCAACAACAACCAGTACGGGGCCATGCAAAACCTGCACGACTCC
TGCTCAAGGCAACTCTATGTTTCCCTCATGTTGCTGTACAAAACCTACGGATG
GAAATTGCACCTGTATTCCCATCCATCGTCCTGGGCTTTCGCAAAATACCTA
TGGGAGTGGGCCTCAGTCCGTTTCTCTTGGCTCAGTTTACTAGTGCCATTTGT
TCAGTGGTTCGTAGGGCTTTCCCCCACTGTTTGGCTTTCAGCTATATGGATGA
TGTGGTATTGGGGGCCAAGTCTGTACAGCATCGTGAGTCCCTTTATACCGCT
GTTACCAATTTTCTTTTGTCTCTGGGTATACATTTAAACCCTAACAAAACAAAA
AGATGGGGTTATTCCCTAAACTTCATGGGTTACATAATTGGAAGKKGGGGAA
CATTGCCACAGGATCATATTGTACAAAAGATCAAACACTGT

Figure 4

STSKRQSSSGHAVEFHCLPPSSAGSQSQGSVFSCWWLQFRNSKPCSEYCLSHL
VNLREDWGPCDEHGEHHIRIPRTPARVTGGVFLVDKNPHNTAESRLVVDFSQFS
RGITRVSWPKFAVPNLQSLTNLLSSNLSWLSLDVSAAFYHIPLHPAAMPHLLIGSS
GLSRYVARLSSNSRINNNQYGAMQNLHDSCSRQLYVSLMLLYKTYGWKLHLYS
HPIVLGFRKIPMGVGLSPFLLAQFTSAICSVVRRAFPHCLAFSYMDDVVLGAKSV
QHRESLYTAVTNFLLSLGIHLNPNKTKRWGYSLNFMGYIIG[R/S][G/W]GTLPQDHI
VQKIKHC

Figure 5

PPLRDSHPQAMQWNSTAFHQALQDPRVRGLYFPAGGSSSGTVNPAPNIASHIS
SISARTGDPVTNMENITSGFLGPLLVLQAGFFLLTRILTIPQSLDSWWTSLNFLGG
SPVCLGQNSQSPTSNHSPTSCPPICPGYRWMCLRRFIIFLFILLLCLIFLLVLLDYQ
GMLPVCPLIPGSTTTSTGPCKTCTTPAQGNSMFPSCCCTKPTDGNCTCIPIPSSW
AFAKYLWEWASVRFSWLSLLVPFVQWFVGLSPTVWLSAIWMMWYWGPSLYSIV
SPFIPLLPIFFCLWVYI

Figure 6

Patient B
ATGCCCCTATCTTATCAACACTTCCGGAAACTACTGTTGTTAGACGACGAGGC
AGGTCCCCTAGAAGAAGAACTCCCTCGCCTCGCAGACGAAGGTCTCAATCGC
CGCGTCGCAGAAGATCTAAATCTCGGGAATCTCAATGTTAGTATCCCTTGGA
CTCATAAGGTGGGAAACTTTACTGGGCTTTATTCTTCTACTGTACCTGTCTTTA
ATCCTGACTGGCAAACTCCCTCTTTTCCTCACATTCATTTGAAAGAGGATATTA
TTGATAGATGTCAACAATATGTAGGCCCTCTTACAGTTAACGAAAAAGGAGA
TTAAAATTGATTATGCCTGCTAGATTCTATCCTAACCGTACCAAATATTTGCCC
TTAGATAAAGGCATTAARCCTTATTATCCTGAACACACAGTTAATCATTACTTC
CAAACTAGGCATTAYTTACATACTCTGTGGAAGGCTGGTATTTTATATAAGAG
AGAAACTACTCGCAGCGCCTCATTCTGTGGGTCACCATATTCTTGGGAACAA
GAGCTACAGCATGGGAGGTTCGTATTCCAAACCTCGACAAGGCATGGGGAC
GAATCTTTCTGTTCCCAATCCTCTGGGATTCTTTCCCGATCACCAGTTGGACC
CGGCATTCAGAGCCAATTCAAACAATCCAGATTGGGACTTCAACCCCAACAA
GGATCAATGGCCKGCGGCACACCAGGTAGGAGTGGGATCCTTCGGGCCAGG
GTTCACTCCACCACACGGCAATCTTTTGGGGTGGAGCCCTCAGGCTCAGGG
CATRTTGACAACAGTRCCAGCRGCGCCTCCTCCTGCCTCCACCAATCGGCAG
TCAGGAAGACAGCCTACTCCCATCTCTCCACCTCTRAGAGACAGTCATCCTC
AGGCCACATTCCACCAAGCTCTGCTAGATCCCAGAGTGAGGGGCCTATACYT
TCCTGCTGGTGGCTCCAGTTCCGGAACAGTRAACCCTGTTCCGACTACTGCC
TCTCCCATATCGTCAATCTTCTCGAGGACTGGGGACCCTGCACCGAAGATGG
AGAGCACCACATCAGGATTCCTAGGACCCCTGCTCGTGTTACAGGCGGGGTT
TTTCTTGTTGACAAGAATCCTCACAATACCACAGAGTCTAGACTCGTGGTGGA
CTTCTCTCAATTTTCTAGGGGGAGCACCCACGTGTCCTGGCCAAAATTTGCA
GTCCCCAACCTCCAATCACTCACCAACCTCTTGTCCTCCAATTTGTCCTGGTT
ATCGCTGGATGTGTCTGCGGCGTTTTATCATATTCCTCTTCATCCTGCTGCTA
TGCCTCAYCTTCTTGTTGGTTCTTCTGGACTAYCAAGGTATGTTGCCCGTTTG
TCCTCTACTTCCAGGAACATCAACYACCAGCACGGGACCATGCAAGACCTGC
ACGACTCCTGCTCAAGGAACCTCTATGTTTCCCTCTTGTTGCTGTACAAAACC
TTCGGACGGAAATTGCACTTGTATTCCCATCCATCATCTTGGGCTTTCGCAA
GATTCCTATGGGAGTGGGCCTCAGTCCGTTTCTCATGGCTCAGTTTTCTAGT
GCCATTTGTTCAGTGGTTCGTAGGGCTTTCCCCCACTGTTTGGCTTTCAGTTA
TGTGGATGATGTGGTATTGGGGGCCAAGTCTGTACAACATCTTGAATCCCTTT
TTACCGCTGTTACCAATTTTCTTTTGTCTTTGGGTATACATTTAAACCCTACTA
AAACTAAACGTTGGGGCTACTCCCTTCACTTCATGGGWTATGTAATTGGAAG
TTGGGGTACCTTACCACAGGAACATATTGTACACAAAATCAAACAATGTTTTC
GGAAACTTCCTATAAATAGACCTATTGATTGGAAAGTATGTCAACGAATTGTG
GGGCTTCTAGGCTTTGCCGCTCCCTTTACACAATGTGGTTACCCAGCATTAAT
GCCTTTGTATGCATGTATACAAGCTAAACAGGCTTTCACTTTTCGCCAACTTA
CAAGGCCTTTCTGTGTAAACAATATCTGCACCTTTACCCCGTTGCTCGGCAAC
GGTCAGGTCTTTGCCAAGTGTTTGCTGACGCAACCCCACTGGTTGGGGCTT
GGCCATAGGCCATCAGCGCMTGCGTGGAACCTTTGTGGCTCCTCTGCCGAT
CCATACTGCGGAACTCCTAGCAGCTTGTTTTGCTCGCAGCCGGTCTGGAGCA

Figure 7a

```
AACATTATCGGCACCGACAACTCTGTTGTCCTCTCTCGGAAATACACCTCCTT
TCCATGGCTGCTAGGCTGTGCTGCCAACTGGATCCTGCGCGGGACGTCCTTT
GTCTACGTCCCGTCRGCGCTGAATCCCGCGGACGACCCGTCTCGGGGCAGG
TTGGGACTCTACCGTCCCCTTCTTCGTCTGCCGTTCCGGCCGACCACGGGG
CGCACCTCTCTTTACGCGGTCTCCCCGTCTGTGCCTTCTCATCTGCCGGACC
GTGTGCACTTCGCTTCACCTCTGCACGTCGCATGGAAACCACCGTGAACGCC
YGCCAGGTCTTGCCCAAGGTCTTACATAAGAGGACTCTTGGACTCTCAGCAA
TGTCAACGACCGACCTTGAGGCATACTTCAAAGACTGTGTATTTACAGACTGG
GAGGAGTTGGGGGAGGAGACTAGGTTAATGATCTTTGTACTAGGAGGCTGTA
GGCATAAATTGGTCTGTTCACCAGCACCATGCAACTTTTTCACCTCTGCCTAA
TCATCTCTTGTTCATGTCCCACTGTTCAAGCCTCCAAGCTGTGCCTTGGGTGG
CTTTGGGGCATGGACATTGACACCTATAAAGAATTTGGAGCTTCTGTGGAGTT
ACTCTCTTTTTTGCCTTCTGACTTCTTTCCGAATATTCGTGATCTCCTCGACAC
CGCCTCTGCTCTGCATCGGGAKGCCTTAGAGTCTCMGGAACATTGTTCMCCT
CACCATACAGCACTAAGGCAAGCTATTGTGTTGGGGTGAGTTGATGAATC
TGGCCACCTGGGTGGGAAGTAATTTGGAAGACCCAGCATCCAGGGAATTAGT
AGTAAGCTATGTCAACGTTAATATGGGCCTAAAAATCAGACAACTATTGTGGT
TTCACATTTCCTGTCTTACTTTTGGAAGAGAAACTGTTCTTGAGTATTTGGTGT
CTTTTGGAGTGTGGATTCGCACTCCTCCCGCTTACAGACCACCAA
```

Figure 7b

MPLSYQHFRKLLLLLDDEAGPLEEELPRLADEGLNRRVAEDLNLGNLNVSIPWTHK
VGNFTGLYSSTVPVFNPDWQTPSFPHIHLKEDIIDRCQQYVGPLTVNEKRRLKLI
MPARFYPNRTKYLPLDKGIKPYYPEHTVNHYFQTRHYLHTLWKAGILYKRETTRS
ASFCGSPYSWEQELQHGRFVFQTSTRHGDESFCSQSSGILSRSPVGPGIQSQF
KQSRLGLQPQQGSMA[G/C]GTPGRSGILRARVHSTTRQSFGVEPSGSGH[I/V]D
NS[T/A]S[S/G]ASSCLHQSAVRKTAYSHLSTS[K/E]RQSSSGHIPPSSARSQSEGPI
[P/L]SCWWLQFRNS[K/E]PCSDYCLSHIVNLLEDWGPCTEDGEHHIRIPRTPARVT
GGVFLVDKNPHNTTESRLVVDFSQFSRGSTHVSWPKFAVPNLQSLTNLLSSNLS
WLSLDVSAAFYHIPLHPAAMPHLLVGSSGL[P/S]RYVARLSSTSRNIN[H/Y]QHGT
MQDLHDSCSRNLYVSLLLLYKTFGRKLHLYSHPIILGFRKIPMGVGLSPFLMAQFS
SAICSVVRRAFPHCLAFSYVDDVVLGAKSVQHLESLFTAVTNFLLSLGIHLNPTKT
KRWGYSLHFMGYVIGSWGTLPQEHIVHKIKQCFRKLPINRPIDWKVCQRIVGLLG
FAAPFTQCGYPALMPLYACIQAKQAFTFSPTYKAFLCKQYLHLYPVARQRSGLC
QVFADATPTGWGLAIGHQR[M/L]RGTFVAPLPIHTAELLAACFARSRSGANIIGTD
NSVVLSRKYTSFPWLLGCAANWILRGTSFVYVPSALNPADDPSRGRLGLYRPLL
RLPFRPTTGRTSLYAVSPSVPSHLPDRVHFASPLHVAWKPP

Figure 8

MESTTSGFLGPLLVLQAGFFLLTRILTIPQSLDSWWTSLNFLGGAPTCPGQNLQS
PTSNHSPTSCPPICPGYRWMCLRRFIIFLFILLLCL[T/I]FLLVLLDYQGMLPVCPLL
PGTSTTSTGPCKTCTTPAQGTSMFPSCCCTKPSDGNCTCIPIPSSWAFARFLWE
WASVRFSWLSFLVPFVQWFVGLSPTVWLSVMWMMWYWGPSLYNILNPFLPLLP
IFFCLWVYI

Figure 9

Patient C
TCCGCCTCCTGCCTCTACCAATCGACAGTCAGGACGGCAGCCTACCCCGCT
GTCTCCACCTCTGAGAATCACTCATCCTCAGGCCATGCAGTGGAACTCCACA
ACCTTCCACCAAACTCTGCAAGATCCCARAGTGAGAGGCCTGKMTCTCCCTG
CTGGTGGCTCCAGTTCAGGAACAGTAAACCCTGTTCCGACTACTGCCTCTCC
CATATCGWCAATCTTCTCGAGGATTGGGGACCCTGCGCTGAACATGGAGAA
CATCACATCAGGATTCCTAGGACCCCTGCTCGTGTTACAGGCGGGGTTTTTC
TTGTTGACAAGAATCCTCACAATACCGCAGAGTCTAGACTCGTGGTGGACTT
CTCTCAATTTTCTAGGGGGAACTACCGTGTGTCTTGGCCAAAATTCGCAGTCC
CCAACCTCCAATCACTCACCAACCTCCTGTCCTCCAACTTGTCCTGGTTATCG
CTGGATGTGTCTGCGGCGTTTTATCATCTTCCTCTTCATCCTGCTGCTATGCC
TCATCTTCTTGTTGGTTCTTCTGGACTATCAAGGTATGTTGCCCGTTTGTCCT
CTAATTCCAGGATCATCAACCACCAGCACGGGACCCTGCAGAACCTGCACGA
CTCCTGCTCAAGGAACCTCTATGTATCCCTCCTGTTGCTGTACAAAACCTTCG
GATGGAAACTGCACCTGTATTCCCATCCATCATCCTGGGCTTTCGGAAAATT
CCTATGGGAGTGGGCCTCAGCCCGTTTCTCTTGGCTCAGTTTACTAGTGCCA
TTTGTTCAGTGGTTCGTAGGGCTTTCCCCCATTGTTTGGCTTTCAGTTATATG
GATGATGTGGTATTGGGGGCCAAGTCTGTATCGCATCTTGAGTCCCTTTTTAC
CGCTGTTACCAATTTTCTTTTGTCTTTGGGTATACATTTAAACCCTAACAAAAC
AAAAARAWGGGGTTATTCTCTAAATTTCATGGGCTATGTC

Figure 10

SASCLYQSTVRTAAYPAVSTSENHSSSGHAVELHNLPPNSARSQSERP[G/V]SP
CWWLQFRNSKPCSDYCLSHI[D/V]NLLEDWGPCAEHGEHHIRIPRTPARVTGGV
FLVDKNPHNTAESRLVVDFSQFSRGNYRVSWPKFAVPNLQSLTNLLSSNLSWLS
LDVSAAFYHLPLHPAAMPHLLVGSSGLSRYVARLSSNSRIINHQHGTLQNLHDSC
SRNLYVSLLLLYKTFGWKLHLYSHPIILGFRKIPMGVGLSPFLLAQFTSAICSVVRR
AFPHCLAFSYMDDVVLGAKSVSHLESLFTAVTNFLLSLGIHLNPNKTK[K/R][R/W]
GYSLNFMGYV

Figure 11

PPASTNRQSGRQPTPLSPPLRITHPQAMQWNSTTFHQTLQDP[K/R]VRGL[D/A/Y
/S]LPAGGSSSGTVNPVPTTASPIS[T/S]IFSRIGDPALNMENITSGFLGPLLVLQAG
FFLLTRILTIPQSLDSWWTSLNFLGGTTVCLGQNSQSPTSNHSPTSCPPTCPGYR
WMCLRRFIIFLFILLLCLIFLLVLLDYQGMLPVCPLIPGSSTTSTGPCRTCTTPAQGT
SMYPSCCCTKPSDGNCTCIPIPSSWAFGKFLWEWASARFSWLSLLVPFVQWFV
GLSPIVWLSVIWMMWYWGPSLYRILSPFLPLLPIFFCLWVYI*

Figure 12

Patient D

TTGTCCTGGTTATCGCTGGATGTGTCTGCGGCGTTTTATCATCTTCCTCTTCA
TCCTGCTGCTATGCCTCATCTTCTTGTTGGTTCTTCTGGACTATCAAGGTATG
TTGCCCGTCTGTCCTCTAGTTCCGAGATCTTCAACCACCAGCGCGGGACAAT
GCAGAACCTGCACGACTACTGCTCAAGGAACCTCTATGTATCCCTCCTGTTG
CTGTACCAAACCTTCGGACGGAAATTGCACCTGTATTCCCATCCCATCATCCT
GGGCTTTCGGAAAATTCCTATGGGAGTGGGCCTCAGTCCGTTTCTCCTGGCT
CAGTTTGCTAGTGCCATTTGTTCAGTGGTTCGTAGGGCTTTCCCCCACTGTTT
GGCTTTCAGTTATATGGATGATGTGGTATTGGGGGCCAAGTCTGTACAACAT
CTTGAGTCCCTTTTTACCGCTGTTACCAATTTTCTTTTGTCTTTGGGTATACAT
TTAAATCCTAACAAAACTAAAAGATGGGGTTACTCTTTAAATTTCATGGGCTAT
GTCATTGGATGTCATGGGTCCTTGCCACAAGATCACATCATACAGAAAATCA

Figure 13

LSWLSLDVSAAFYHLPLHPAAMPHLLVGSSGLSRYVARLSSSSEIFNHQRGTMQ
NLHDYCSRNLYVSLLLLYQTFGRKLHLYSHPIILGFRKIPMGVGLSPFLLAQFASAI
CSVVRRAFPHCLAFSYMDDVVLGAKSVQHLESLFTAVTNFLLSLGIHLNPNKTKR
WGYSLNFMGYVIGCHGSLPQDHIIQKI

Figure 14

CPGYRWMCLRRFIIFLFILLLCLIFLLVLLDYQGMLPVCPLVPRSSTTSAGQCRTCT
TTAQGTSMYPSCCCTKPSDGNCTCIPIPSSWAFGKFLWEWASVRFSWLSLLVPF
VQWFVGLSPTVWLSVIWMMWYWGPSLYNILSPFLPLLPIFFCLWVYI

Figure 15

Patient E
CTACCAATCGACAGTCAGGGAGGCAGCCTACCCCGCTGTCTCCACCTTTGAG
AAACACTCATCCTCAGGCCATGCAGTGGAACTCCACAACTTTCCACCAAACTC
TACAAGATCCCAGGGTGAGAGGCCTGTATTTCCCTGCTGGTGGCTCCAGTTC
AGGAACAGTAAACCCTGTTCCGACTACTGCCTCTCCCATATCGTCAATCTTCT
CGAGGATTGGGGACCCTGCGCTGAACATGGAGAACATCACATCAGGATTCCT
AGGACCCCTGCTCGTGTTACAGGCGGGGTTTTCTTGTTGACAAAAATCCTC
ACAATACCGCAGAGTCTAGACTCGTGGTGGACTTCTCTCAATTTTCTAGGGG
GAACCACCGTGTGTCTTGGCCAAAATTCGCAGTCCCCAACCTCCAATCACTC
ACCAACCTCCTGTCCTCCGACTTGTCCTGGTTATCGCTGGATGTGTCTGCGG
CGTTCTATCATATTCCTCTTCATCCTGCTGCTATGCCTCATCTTCTTGTTGGTT
CTTCTGGACTATCAAGGTATGTTGCCCGTCTGTCCTCTAATTCCAGGATCKTC
AACCACCAGCGCGGGACCATGCAGAACCTGCACGACTACTGCTCAAGGAAC
CTCTATGTATCCTCCTGTTGTTGTACCAAACCTTCGGACGGAAATTGCACCT
GTATTCCCATCCCATCATCCTGGGCTTTCGGAAAATTCCTATGGGAGTGGGC
CTCAGCCCGTTTCTCCTGGCTCAGTTTACTAGTGCCATTTGTTCAGTGGTTCG
TAGGGCTTTCCCCCACTGTTTGGCTTTCAGTTATATGGATGATGTGGTATTGG
GGGCCAAGTCTGTTCAGCMTCGTGAAGCCCTTTTTACCGCTGTTACCAATTTT
CTTWTGTCTTTGGGTAYACATTTAAACCCTAACAAAAMTAGAAGATGGGGTTA
TTCCTTAAATTTCATGGGCT

Figure 16

YQSTVREAAYPAVSTFEKHSSSGHAVELHNFPPNSTRSQGERPVFPCWWLQFR
NSKPCSDYCLSHIVNLLEDWGPCAEHGEHHIRIPRTPARVTGGVFLVDKNPHNTA
ESRLVVDFSQFSRGNHRVSWPKFAVPNLQSLTNLLSSDLSWLSLDVSAAFYHIPL
HPAAMPHLLVGSSGLSRYVARLSSNSRI[V/F]NHQRGTMQNLHDYCSRNLYVSLL
LLYQTFGRKLHLYSHPIILGFRKIPMGVGLSPFLLAQFTSAICSVVRRAFPHCLAFS
YMDDVVLGAKSVQ[H/P]REALFTAVTNFL[M/L]SLG[T/I]HLNPNK[N/T]RRWGYSL
NFMG

Figure 17

TNRQSGRQPTPLSPPLRNTHPQAMQWNSTTFHQTLQDPRVRGLYFPAGGSSS
GTVNPVPTTASPISSIFSRIGDPALNMENITSGFLGPLLVLQAGFFLLTKILTIPQSL
DSWWTSLNFLGGTTVCLGQNSQSPTSNHSPTSCPPTCPGYRWMCLRRSIIFLFI
LLLCLIFLLVLLDYQGMLPVCPLIPGSSTTSAGPCRTCTTTAQGTSMYPSCCCTKP
SDGNCTCIPIPSSWAFGKFLWEWASARFSWLSLLVPFVQWFVGLSPTVWLSVIW
MMWYWGPSLFS[I/L]VKPFLPLLPIF[L/F]CLWV[H/Y]I*

Figure 18

Patient F

CTCCACCACGTTCCACCAAACTCTTCAAGATCCCAGAGTCAGGGCCCTGTAC
TTTCCTGCTGGTGGCTCCAGTTCAGGAACAGTGAGCCCTGCTCAGAATACTG
TCTCTGCCATATCGTCAATCTTATCGAAGACTGGGGACCCTGTACCGAACAT
GGAGAACATCGCATCAGGACTCCTAGGACCCCTGCTCGTGTTACAGGCGGG
GTTTTTCTCGTTGACAAAAATCCTCACAATACCACAGAGTCTAGACTCGTGGT
GGACTTCTCTCAATTTTCTAGGGGAAACACCCGTGTGTCTTGGCCAAAATTCG
CAGTCCCAAATCTCCAGTCACTCACCAACCTGTTGTCCTCCAATTTGTCCTGG
TTATCGCTGGATGTGTCTGCGGCGTTTTATCATCTTCCTCTGCATCCTGCTGC
TATGCCTCATCTTCTTGTTGGTTCTTCTGGACTATCAAGGTATGTTGCCCGTTT
GTCCTCTAATTCCAGGATCATCAACGACCAGCACCGGACCATGCAAAACCTG
CACAACGCCTGCTCAAGGAACCTCTATGTTWCCCTCATGTTGCTGTACAAAA
CCTACGGACGGAAACTGCACCTGTATTCCCATCCCATCATCTTGGGCTTTCG
CAAAATACCTATGGGAGTGGGCCTCAGTCCGTTTCTCATGGTTCAGTTTACTA
GTGCCATTTGTTCAGTGGTTCGTAGGGCTTTCCCCCACTGTCTGGCTTTCAGT
TATATGGATGATGTGGTTTTGGGGGCCAAGTCTGTACAACMTCTTGASTCCCT
TTATGCCGCTGTTACCAATTTTCTTCTGTCTTTGGGTATACATTTAAACCCTGA
CAAAACAAAAARAKGGGGATATTCCCTCAACTTCATGGGATATGTAWTTGGG
AGTTGGGGCACATTGCCACAGGAACATATTGTMCAAAAAATCAA

Figure 19

LHHVPPNSSRSQSQGPVLSCWWLQFRNSEPCSEYCLCHIVNLIEDWGPCTEHG
EHRIRTPRTPARVTGGVFLVDKNPHNTTESRLVVDFSQFSRGNTRVSWPKFAVP
NLQSLTNLLSSNLSWLSLDVSAAFYHLPLHPAAMPHLLVGSSGLSRYVARLSSNS
RIINDQHRTMQNLHNACSRNLYV[T/S]LMLLYKTYGRKLHLYSHPIILGFRKIPMGV
GLSPFLMVQFTSAICSVVRRAFPHCLAFSYMDDVVLGAKSVQ[H/P]L[D/E]SLYAA
VTNFLLSLGIHLNPDKTK[K/R][G/W]GYSLNFMGYV[I/F]GSWGTLPQEHIVQKI

Figure 20

STTFHQTLQDPRVRALYFPAGGSSSGTVSPAQNTVSAISSILSKTGDPVPNMENI
ASGLLGPLLVLQAGFFSLTKILTIPQSLDSWWTSLNFLGETPVCLGQNSQSQISSH
SPTCCPPICPGYRWMCLRRFIIFLCILLLCLIFLLVLLDYQGMLPVCPLIPGSSTTST
GPCKTCTTPAQGTSM[L/F]PSCCCTKPTDGNCTCIPIPSSWAFAKYLWEWASVR
FSWFSLLVPFVQWFVGLSPTVWLSVIWMMWFWGPSLYN[I/L]L[T/S]PFMPLLPIF
FCLWVYI*

Figure 21

Patient G

CAGCGAGCCCTGCTCAGAATACTGTCTCTGCCATATCGTCAATCTTATCGAAG
ACTGGGGACCCTGTACCGAACATGGAGAACATCGCATCAGGACTCCTAGGA
CCCCTGCTCGTGTTACAGGCGGGGTTTTTCTTGTTGACAAAAATCCTCACAAT
ACCACAGAGTCTAGACTCGTGGTGGACTTCTCTCAATTTTCTAGGGGGGACA
CCCGTGTGTCTTGGCCAAAATTCGCAGTCCCAAATCTCCAGTCACTCACCAA
CTTGTTGTCCTCCAACTTGTCCTGGTTATCGCTGGATGTATCTGCGGCGTTTT
ATCATCTTCCTCTGCATCCTGCTGCTATGCCTCATCTTCTTGTTGGTTCTTCTG
GACTATCAAGGTATGTTGCCCGTATGTCCTCTAATTCCAGGATCATCAACAAC
CAGCACCGGACCATGCAAAACCTGCACGACTCCTGCTCAAGGAACCTCTATG
TTTCCCTCATGTTGCTGTACAAAACCTACGGACGGAAACTGCACCTGTATTCC
CATCCCATCATCTTGGGCTTTCGCAAAATACCTATGGGAGTGGGCCTCAGTC
CGTTTCTCTTGGYTCAGTTTACTAGTGCCATTTGTTCAGTGGTTCGTAGGGCT
TTCCCCCACTGTCTGGCTTTCAGTTATATGGATGATGTGGTTTTGGGGGCCAA
GTCTGCACAACATCTTGAGTCCCTTYATGCCGCTGTTACCAATTTTCTTTTGTC
TTTGGGTATACATTTAACCCCTCA

Figure 22

SEPCSEYCLCHIVNLIEDWGPCTEHGEHRIRTPRTPARVTGGVFLVDKNPHNTTE
SRLWDFSQFSRGDTRVSWPKFAVPNLQSL TNLLSSNLSWLSLDVSAAFYHLPL
HPAAMPHLLVGSSGLSRYVARMSSNSRIINNQHRTMQNLHDSCSRNL YVSLMLL
YKTYGRKLHLYSHPIILGFRKIPMGVGLSPFLL[A/V]QFTSAICSVVRRAFPHCLAF
SYMDDWLGAKSAQHLESL[HN]AAVTNFLLSLGIHL TP

FIGURE 23

ASPAQNTVSAISSILSKTGDPVPNMENIASGLLGPLLVLQAGFFLL TKIL TIPQSLDS
WWTSLNFLGGTPVCLGQNSQSQISSHSPTCCPPTCPGYRWMYLRRFIIFLCILLL
CLIFLLVLLDYQGMLPVCPLIPGSSTTSTGPCKTCTTPAQGTSMFPSCCCTKPTD
GNCTCIPIPSSWAFAKYLWEWASVRFSW[L/F]SLLVPFVQWFVGLSPTVWLSVIW
MMWFWGPSLHNILSPFMPLLPIFFCLWVYI

Figure 24

Patient H

GAGGATTGGGGACCCTGCGCTGAA TATGGAGAACATCACATCAGGA TTCCTA
GGACCCCTTCTCGTGTTACAGGCGGGGTTTTTCTTGTTGACAAGAA TCCTCA
CAA TACCGCAGAGTCTAGASTCGTGGTGGACTTCTCTCAA TTTTCTAGGGGSA
ACCACCGTGTGTCTTGGCCAAAATTCGCAGTCCCCAACCTCCAATCACTCAC
CAACCTCCTGTCCTCCGACTTGACCTGGTTATCGCTGGATGTGACTGCGGCA
TTTTATCATATTCCTCTTCATCCTGCTGCTATGCCTCATCTTCTTGTTGGTTCT
TCTGGACTATCAAGGTATGTTGCCCGTTTGTCCTCT AA TTCCAGGATCCTCAA
CCACCAGCACGGGAACATGCCGAACTTGCACGACTCCTGCTCAAGGAACCT
CTATGTATCCCTCCTGTTGCTGTACCAAACCTTCGGACGGAAATTGCACCTGT
ATTCCCATCCCATCATCCTGGGCTTTCGGAAAA TTCCTATGGGAGTGGGCCT
CAGCCCGTTTCTCATGGCTCAGTTTGGTAGTGCCA TTTGTTCAGTGGTTCGTA
GGGCTTTCCCCCACTGTTTGGCTTTCATTT ATGTGGATGATRTGGTATTGGGG
GCCAAGTCTGTACAGCATCTTGAGTCCCTTTTTACCGCTGTTACCAATTTTCTT
TTGTCTCTGGGTATACATTTGRWCCCTMACAAAACAAAGAGATGGGGTT ACT
CCCT AAA TTTT ATGGGCTATGTCATTGGATGTT ATGGGTCCTTGCCACAAGAA
CACATCATACATAAAATCAAAGAATGTTT

Figure 25

EDWGPCAEYGEHHRIPRTPSRVTGGVFLVDKNPHNTAESR[LN]WDFSQFSRG
NHRVSWPKFAVPNLQSLTNLLSSDLπVLSLDVTAAFYHIPLHPAAMPHLLVGSSG
LSRYVARLSSNSRILNHQHGNMPNLHDSCSRNLYVSLLLLYQTFGRKLHLYSHPII
LGFRKIPMGVGLSPFLMAQFGSAICSWRRAFPHCLAFIYVDD[M/V]VLGAKSVQ
HLESLFTAVTNFLLSLGIHL[N/I/D/V]P[N/H]KTKRWGYSLNFMGYVIGCYGSLPQE
HHKIKEC

Figure 26

MENITSGFLGPLLVLQAGFFLLTRILTIPQSL[D/E]SWVVTSLNFLG[A/G]TTVCLGQ
NSQSPTSNHSPTSCPPT*PGYRWM*LRHFIIFLFILLLCLIFLLVLLDYQGMLPVCPL
IPGSSTTSTGTCRTCTTPAQGTSMYPSCCCTKPSDGNCTCIPIPSSWAFGKFLW
ENASARFSWLSLWPFVQWFVGLSPTVWLSFMWM[I/M]WYWGPSL YSILSPFLP
LLPIFFCLWVYI[*/W]

Figure 27

Patient I
nucleotide (nt rt181 to rt863)

ATCGCAGTCCCCAACCTCCAATCACTCACCAACCTCCTGTCCTCCAACTTGAC
CTGGTT ATCGCTGGATRTGTCTGCGGCGTTTT ATCATCTTCCTCTTCATCCTG
CTGCTATGCCTCATCTTCTTGTTGGTTCTTCTGGACTATCAAGGTATGTTGCC
CGTTTGTCCTCT AA TTCCAGGATCMTCAACCACCAGCACGGGACCATGCAGR
ACCTGCACGACTCCTGCTCAAGGAACCTCTATGAATCCCTCCTGTTGCTGTW
CCRAACCTTCGGACGGAAA TTGCACCTGTA TTCCCATCCCATCATCCTGGGC
TTTCGGAAAATTCCTATGGGAGTGGGCCTCAGCCCGTTTCCTGGCTCART
TT ACTAGTGCYA TTTGTTCAGTGGTTCGTAGGGCTTTCCCCCACTGTKTGGCT
TTCAGTT AT ATRGATGATGTGGTA TTGGGGGCCAAGTCTGTACAGCATCTTGA
GKCCCTTTWT ACCGCTGTT ACCAATTTTCTTTTGTCTCTGGGTAYACA TTTAAA
CCCTCACAAAACAAAAAGATGGGGTT ACYMTTT ACA TTTCATGGGCTATGTCA
TTGGATGTTATGGGTCA TTGCCACAAGATCACA TCAKACAGAAAA TCAAAGAA
TGTTTT AGAAAACTTCCTGTT AA TAGGCCTA TTGA TTGGAAAGTATGTCA

Figure 28

POL translaion (aa rt61 to287)

IAVPNLQSLTNLLSSNL TWLSLD[MN]SAAFYHLPLHPAAMPHLLVGSSGLSRYVA
RLSSNSRI[I/L]NHQHGTMQ[N/D]LHDSCSRNL YESLLLL[Y/F][Q/R]TFGRKLHL YS
HPILGFRKIPMGVGLSPFLLAQFTSAICSWRRAFPHC[V/L]AFSY[I/M]DDWLGA
KSVQHLE[A/S]L[Y/F]TAVTNFLLSLG[T/I]HLNPHKTKRWGY[H/P/Y/S]LHFMGYVI
GCYGSLPQDHI[R/I]QKIKECFRKLPVNRPIDWKVC

Figure 29

Env translaion (aa s53 to end)

SQSPTSNHSPTSCPPT*PGYRW[I/M]CLRRFIIFLFILLLCLIFLLVLLDYQGMLPVC
PLIPGSSTTSTGPCRTCTTPAQGTSMNPSCCC[T/S][K/E]PSDGNCTCIPIPSSWA
FGKFLWEWASARFSWL[N/S]LLV[P/L]FVQWFVGLSPTVWLSVI[*/W]MMWYWGP
SLYSIL[R/S]PF[I/L]PLLPIFFCLWV[H/Y]I*

Figure 30

DETECTION AND USE OF ANTIVIRAL RESISTANCE MUTATIONS

This application is U.S. National Phase of International Application PCT/AU2007/000785, filed Jun. 4, 2007 designating the U.S., and published in English as WO 2007/140522 on Dec. 13, 2007, which claims priority to Australian Patent Application No. 2006903065 filed Jun. 6, 2006.

FIELD

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. Vaccines and diagnostic assays are also contemplated herein.

BACKGROUND

Bibliographic details of the publications referred to in this specification are also collected at the end of the description.

The reference to any prior art in this specification is not, and should not be taken as, an acknowledgment or any form of suggestion that that prior art forms part of the common general knowledge in any country.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, *Cell* 29:403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of HBV overlaps the envelope gene, mutations in the catalytic domain of the polymerase gene can also affect the nucleotide and the deduced amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside or nucleotide analogs could act as effective anti-viral agents. Examples of nucleoside or nucleotide analogs currently being tested are penciclovir and its oral form (FCV) [Vere Hodge, *Antiviral Chem Chemother* 4: 67-84, 1993; Boyd et al, *Antiviral Chem Chemother.* 32:358-363, 1987; Kruger et al, *Hepatology* 22:219 A, 1994; Main et al, *J. Viral Hepatitis* 3:211-215, 1996], Lamivudine [(−)-β-2'-deoxy-3'-thiacytidine]; (3TC or LMV) [Severini et al, *Antimicrobial Agents Chemother.* 39:430-435, 1995; Dienstag et al, *New England J Med* 333:1657-1661, 1995]. New nucleoside or nucleotide analogs which have already progressed to clinical trials include the pyrimidines Emtricitabine, ((−)-β-L-2'-3'-dideoxy-5-fluoro-3'-thiacydidine; FTC), the 5-fluoro derivative of 3TC, and Clevudine (1-(2-fluoro-5-methyl-β-L-arabino-furanosyl) uracil; L-FMAU), a thymidine analog. The beta-L thymidine analogue (LdT has recently been given FDA approval other similar compounds include beta-L-2'-deoxycytidine (LdC) and beta-L-2'-deoxyadenosine (LdA) [Standring et al., *Antivir Chem Chemother.* 2001; 12 Suppl 1:119-29]. Like 3TC, these are pyrimidine derivatives with an unnatural "L"—configuration. Several purine derivatives have also progressed to clinical trials; they include Entecavir (BMS-200, 475; ETV), a carbocyclic deoxyguanosine analog, diaminopurine dioxolane (DAPD), an oral pro-drug for dioxolane guanine ((−)-β-D-2-aminopurine dioxolane; DXG) and Adefovir dipivoxil, an oral prodrug for the acyclic deoxyadenosine monophosphate nucleoside or nucleotide analog Adefovir (9-[phosphoryl-methoxyethyl]-adenine; PMEA). Other drugs in pre-clinical and clinical trials include FLG [Medivir], ACH-126,443 (L-d4C) [Archillion Pharmaceuticals], ICN 2001-3 (ICN) and Racivir (RCV) [Pharmassett].

Whilst these agents are highly effective in inhibiting HBV DNA synthesis, there is the potential for resistant mutants of HBV to emerge during long term antiviral chemotherapy. In patients on prolonged LMV therapy, key resistance mutations are selected in the rt domain within the polymerase at rtM204I/V+/−rtL180M as well as other mutations. The nomenclature used for the polymerase mutations is in accordance with that proposed by Stuyver et al, 2001, supra. LMV is a nucleoside or anucleotide analog that has been approved for use against chronic HBV infection. LMV is a particularly potent inhibitor of HBV replication and reduces HBV DNA titres in the sera of chronically infected patients after orthotopic liver transplantation (OLT) by inhibiting viral DNA synthesis. LMV monotherapy seems unlikely to be able to control HBV replication in the longer term. This is because emergence of LMV-resistant strains of HBV seems almost inevitable during monotherapy.

Adefovir dipivoxil (ADV: formerly, bis-pom PMEA) is an orally available prodrug of the acyclic deoxyadenosine monophosphate analog adefovir (formerly, PMEA) (FIG. 2). ADV is also a potent inhibitor of HBV replication and has been given FDA approval for use against chronic HBV infection. Adefovir dipivoxil differs from other agents in this class in that it is a nucleotide (vs. nucleoside) analog and as such bypasses the first phosphorylation reaction during drug activation. This step is often rate-limiting. Adefovir dipivoxil has demonstrated clinical activity against both wild-type and lamivudine-resistant strains of HBV and is currently in phase III clinical Testing (Gilson et al, *J Viral Hepat* 6:387-395, 1999; Perrillo et al, *Hepatology* 32:129-134, 2000; Peters et al, *Transplantation* 68:1912-1914, 1999; Benhamou et al, *Lancet* 358:718-723, 2001). During phase II studies a 30 mg daily dose of adefovir dipivoxil resulted in a mean 4 $\log_{10}$ decrease in viremia over 12 weeks (Heathcote et al, *Hepatology* 28:A620, 1998).

ADV is a substituted acyclic nucleoside phosphonate. This class of compounds also includes tenofovir disoproxil fumarate (also referred to as tenofovir DF, or tenofovir, or (TFV) or 9-R-(2-phosphonomethoxypropyl)adenine (PMPA) and is marketed as Viread by Gilead sciences).

TFV has antiviral activity against both HBV and HIV (Ying et al, *J Viral Hepat.* 7(2):161-165, 2000; Ying et al, *J. Viral Hepat.* 7(1):79-83, 2000, Suo et al, *J Biol Chem.* 273 (42):27250-27258. 1998).

FTC has activity against HBV and HIV (Frick et al, *Antimicrob Agents Chemother* 37:2285-2292, 1993).

LdT, LdC and LdA have activity against HBV (Standring et al, in supra)

Nucleoside or nucleotide analog therapy may be administered as monotherapy or combination therapy where two or more nucleoside or nucleotide analogs may be administered. The nucleoside or nucleotide analogs may also be administered in combination with other antiviral agents such as interferon or hepatitis B immunoglobulin (HBIG).

There is a need to monitor for the emergence of nucleoside/nucleotide-analog- or antibody-resistant strains of HBV and to develop diagnostic protocols to detect these resistant viruses and/or to use them to screen for and/or develop or design agents having properties making them useful as antiviral agents. Defective forms of these resistant strains or antigenic components therefrom are also proposed to be useful in the development of therapeutic vaccine compositions as are antibodies directed to viral surface components.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

Specific mutations in an amino acid sequence are represented herein as "$Xaa_1nXaa_2$" where $Xaa_1$ is the original amino acid residue before mutation, n is the residue number and $Xaa_2$ is the mutant amino acid. The abbreviation "Xaa" may be the three letter or single letter (i.e. "X") code. An "rt" before "$Xaa_1nXaa_2$" means "reverse transcriptase". An "s" means an envelope gene. The amino acid residues for HBV DNA polymerase are numbered with the residue methionine in the motif Tyr Met Asp Asp (YMDD) being residue number 204 (Stuyver et al, *Hepatology* 33:751-757, 2001). The amino acid residues for hepatitis B virus surface antigen are number according to Norder et al, (*J. Gen. Virol.* 74:341-1348, 1993). Both single and three letter abbreviations are used to define amino acid residues and these are summarized in Table 2.

The selection of HBV variants is identified in patients with chronic HBV infection treated with antiviral agents including nucleosides and nucleotide analogs including TFV and/or LMV, or LMV and/or ADV and/or ETV. Consequently, HBV rt variants are contemplated which are resistant to, or which exhibit reduced sensitivity to antiviral agents including nucleosides and nucleotide analogs including, ADV, LMV, TFV, ETV or FTC, or LdT; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combinations thereof. Corresponding mutations in the surface antigen also occur. The identification of these HBV variants is important for the development of assays to monitor ADV, LMV, FTC, TFV, LdT and/or ETV resistance and/or resistance to other nucleoside or nucleotide analogs or other anti-HBV agents or combinations thereof and to screen for agents which are useful as alternative therapeutic agents.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside or nucleotide analog or other anti-HBV agents or combinations thereof. The clinician is then able to modify an existing treatment protocol or select an appropriate treatment protocol accordingly.

Accordingly, one aspect is directed to an isolated Hepatitis B virus (HBV) variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV, ETV, LdT or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. The variant HBV comprises a mutation in an overlapping open reading frame in its genome in a region defined by one or more of domains F and G and domain A through to E of HBV DNA polymerase.

Another aspect provides an isolated HBV variant comprising a nucleotide mutation in the S gene resulting in at least one amino acid addition, substitution and/or deletion to the surface antigen and which exhibits decreased sensitivity to one or more nucleoside or nucleotide analogs selected from the list consisting of ADV, LMV, TFV, ETV, or LdT or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof:

Useful mutants in the rt region include, in one embodiment includes, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent mutation.

Particularly useful mutants are co-mutations at codons 180, 184 and 204 such as rtL180M and rtT184S and rtM204V, or co-mutations at codons 85, 180, 184, 202, 204 and 236 such as rtS85T, rtL180M, rtT184G, rtS202I, rtM204V and rtN236I/D/V. Alternative useful mutations contemplated herein include rtP170H, rtT184A, rtY221H/Y, rtI233T/I, rtT240N/T, rtK241R, rtR242K/R, rtW243R/W, rtI253V, rtI254I/F, rtS256R/S rtW257G/W, rtY257H or mutations at codon 239.

Mutations in the putative tri-phosphate binding site at rtN236T region are proposed herein to be important in antiviral resistance against ADV and/or TFV and/or other nucleoside or nucleotide treatments. Important codons apart from codons 236 include codons 239 which is highly conserved and codons 240, 241, 242 and 243.

In a particular embodiment, an isolated Hepatitis B virus (HBV) variant is provided wherein said variant comprises a nucleotide mutation in a gene encoding a DNA polymerase resulting in at least one amino acid addition, substitution and/or deletion to said DNA polymerase wherein the mutation is selected from the group consisting of:
(i) a mutation at codon 239, 240, 241, 242 and/or 243;
(ii) a mutation resulting in an N236I/D/V substitution;
(iii) a mutation resulting in an S246H/P/Y/S substitution;
(iv) a mutation resulting in a P170H substitution;
(v) a mutation resulting in an I253V substitution;
(vi) co-mutations of two or more substitutions selected from the list consisting of rtL42L/V, rtS78T, rtS85T, rtT128N, rtL180M, rtT184G, rtS202I, rtM204V and rtN236I/D/V;
(vii) co-mutations of two or more substitutions selected from the list consisting of rtF61L, rtS78T, rtV84M/V, rtV142E, rtQ149Q/R, rtM204I/M, rtI233T/I and rtS246H/P/Y/S; and
(viii) co-mutations of two or more substitutions selected from the list consisting of rtI29L, rtY50S, rtP170H, rtL180M, rtM204V and rtI253V;
wherein the HBV variant exhibits decreased sensitivity to a nucleoside or nucleotide analog.

Useful mutations in the S gene include, in one embodiment include sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or a combination thereof or an equivalent mutation.

Particularly useful mutants are sI110V, sP120Q, sF134L/F, sL162I, sL173F, sL175F, sL176V and sP178P/L.

A method is further contemplated for determining the potential for an HBV to exhibit reduced sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof by isolating DNA or corresponding mRNA from the HBV and screening for a mutation in the nucleotide sequence encoding HBV DNA polymerase resulting in at least one amino acid substitution, deletion and/or addition in any one or more of domains F and G and domains A through to E or a region proximal thereto of the DNA polymerase and associated with resistance or decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

The presence of such a mutation is an indication of the likelihood of resistance to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Also provided is a composition comprising a variant HBV resistant to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof or an HBV surface antigen from the variant HBV or a recombinant or derivative form thereof or its chemical equivalent and one or more pharmaceutically acceptable carriers and/or diluents.

Yet another aspect provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ADV, LMV, TFV, LdT, ETV or FTC; ADV and LMV; ADV and TFV; LMV and TFV; FTC and ADV; FTC and TFV; FTC and LMV;

ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof in the manufacture of a medicament for the treatment and/or prophylaxis of hepatitis B virus infection.

Also contemplated is a method for determining whether an HBV strain exhibits reduced sensitivity to a nucleoside or nucleotide analog or other anti-HBV agents or by isolating DNA or corresponding mRNA from the HBV and screening for a mutation in the nucleotide sequence encoding the DNA polymerase wherein the presence of the following mutations in the rt region: in one embodiment includes, rtS256R/S and rtW257G/W, in another embodiment includes rtH9D, rtL180M, rtM204V, rtT184S and rtN238T, or yet another embodiment includes rtQ215S, rtR242K/R and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent one or more other mutation is indicative of a variant which exhibits a decreased sensitivity to ADV, LMV, TFV, LdT, ETV or FTC; ADV and LMV; ADV and TFV; LMV and Thy; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Still a further methodology comprises screening for a mutation in the nucleotide sequence encoding the envelope genes (s) wherein the presence of the following mutations in the s gene: in one embodiment include sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment include sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or combinations thereof or an equivalent one or more other mutation is indicative of a variant which exhibits a decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and/or optionally other nucleoside or nucleotide analogs or other anti-HBV agents or combination thereof.

In a particular embodiment, the variants are in an isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions.

Another aspect is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to the HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside or nucleotide analog or other anti-HBV agents of the HBV DNA polymerase. The variant HBV of this aspect of the invention may also comprise a nucleotide sequence comprising a single or multiple nucleotide substitution, addition and/or deletion compared to a pre-treatment HBV.

Further contemplated is a method for detecting a variant HBV exhibiting an altered immunological profile said method comprising isolating an HBV from a subject exposed to a nucleoside or nucleotide analog or combination of analogs selected from the listed consisting of ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting said HBV with a panel of one or more antibodies to a surface antigen and screening for any change in binding affinity or binding spectrum.

In a related aspect, a method is provided for detecting a variant HBV exhibiting an altered immunological profile said method comprising isolating a serum sample from a subject exposed to a nucleoside or nucleotide analog selected from the listed consisting of ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum.

An isolated HBsAg is provided or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

Another aspect contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and the subjecting the cells, cell lysates or culture supernatant fluid to viral- or viral-component-detection means to determine whether or not the virus has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and then subjecting the cells, cell lysates or culture supernatant fluid to viral- or viral-component-detection means to determine whether or not the virus has replicated, expressed genetic material and/or assembled and/or been released in the presence of the agent.

In connection with these methods, the plasmid vector may include genes encoding part or all of other viral vectors such as baculovirus vectors or adenovirus vectors (see Ren and Nassal, *J. Virol.* 75(3):1104-1116, 2001).

In an alternative embodiment, the method comprises generating a continuous cell line comprising an infectious copy of the genome of the HBV in a replication competent effective amount such that said infectious HBV genome is stably integrated into said continuous cell line such as but not limited to the 2.2.15 or AD cell line, contacting the cells with the agent to be tested, culturing the cells for a time and under conditions sufficient for the HBV to replicate, express genetic sequences and/or assemble and/or release virus or virus-like particles if resistant to the agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, a method is contemplated for detecting an agent which exhibits inhibitory activity to an HBV polymerase in an in vitro polymerase assay. The HBV polymerase activity can be examined using established assays (Gaillard et al, *Antimicrob Agents Chemother.* 46(4):1005-1013, 2002; Xiong et al, *Hepatology,* 28(6):1669-73, 1998). The HBV polymerase may be a wild-type or reference HBV polymerase or mutant HBV polymerase.

The identification of viral variants enables the production of vaccines comprising particular recombinant viral components such as polymerases or envelope genes PreS1, PreS2, S encoding for L, M, S proteins as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential. In addition, defective HBV variants may also be used as therapeutic compositions to generate an immune response against the same, similar or homologous viruses. Alternatively, antibodies generated to the HBV variants or surface components thereof may be used in passive immunization of subjects against infection by HBV variants or similar or homologous viruses. Furthermore, agents such as nucleoside or nucleotide analogs, RNAi or siRNA molecules (both DNA-derived or synthetic), antisense or sense oligonucleotides, chemical or proteinaceous molecules having an ability to down-regulate the activity of a component of HBV and inhibit replication, maintenance, infection, assembly or release are contemplated by the present invention.

A summary of the abbreviations used throughout the subject specification are provided in Table 3.

A summary of sequence identifiers used throughout the subject specification is provided in Table 1.

TABLE 1

Summary of sequence identifiers

| SEQUENCE ID NO: | DESCRIPTION |
|---|---|
| 1 | PCR primer OSI 5' |
| 2 | PCR primer TTA3 5' |
| 3 | PCR primer JM 5' |
| 4 | PCR primer TTA4 5' |
| 5 | PCR primer OS2 5' |
| 6 | Nucleotide sequence of catalytic region of polymerase from resistant HBV Patient A |
| 7 | Deduced amino acid sequence of catalytic region of polymerase resistant HBV Patient A |
| 8 | Deduced amino acid sequence of envelope gene from resistant HBV from Patient A |

TABLE 1-continued

Summary of sequence identifiers

| SEQUENCE ID NO: | DESCRIPTION |
|---|---|
| 9 | Nucleotide sequence of catalytic region of polymerase from resistant HBV Patient B |
| 10 | Deduced amino acid sequence of envelope gene from resistant HBV from Patient B |
| 11 | Deduced amino acid sequence of envelope gene from resistant HBV from Patient B |
| 12 | Nucleotide sequence of catalytic region of polymerase from resistant HBV Patient C |
| 13 | Deduced amino acid sequence of catalytic region of polymerase resistant HBV Patient C |
| 14 | Deduced amino acid sequence of envelope gene from resistant HBV from Patient C |
| 15 | Nucleotide sequence of catalytic region of polymerase from resistant HBV Patient D |
| 16 | Deduced amino acid sequence of catalytic region of polymerase resistant HBV Patient D |
| 17 | Deduced amino acid sequence of envelope gene from resistant HBV from Patient D |
| 18 | Nucleotide sequence of catalytic region of polymerase from resistant HBV Patient E |
| 19 | Deduced amino acid sequence of catalytic region of polymerase resistant HBV Patient E |
| 20 | Deduced amino acid sequence of envelope gene from resistant HBV from Patient E |
| 21 | Nucleotide sequence of catalytic region of polymerase from resistant HBV Patient F |
| 22 | Deduced amino acid sequence of catalytic region of polymerase resistant HBV Patient F |
| 23 | Deduced amino acid sequence of envelope gene from resistant HBV from Patient F |
| 24 | Nucleotide sequence of catalytic region of polymerase from resistant HBV Patient G |
| 25 | Deduced amino acid sequence of catalytic region of polymerase resistant HBV Patient G |
| 26 | Deduced amino acid sequence of envelope gene from resistant HBV from Patient G |
| 27 | Nucleotide sequence of catalytic region of polymerase from resistant HBV Patient H |
| 28 | Deduced amino acid sequence of catalytic region of polymerase resistant HBV Patient H |
| 29 | Deduced amino acid sequence of envelope gene from resistant HBV from Patient H |
| 30 | Nucleotide sequence of catalytic region of polymerase from resistant HBV Patient I |
| 31 | Deduced amino acid sequence of catalytic region of polymerase resistant HBV Patient I |
| 32 | Deduced amino acid sequence of envelope gene from resistant HBV from Patient I |

TABLE 2

Single and three letter amino acid abbreviations

| Amino Acid | Three-letter Abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

TABLE 3

Abbreviations

| ABBREVIATION | DESCRIPTION |
|---|---|
| 3TC | (LMV); (−)-β-2'-deoxy-3'-thiacytidine |
| ADV | adefovir dipivoxil |
| DAPD | diaminopurine dioxalone |
| DXG | dioxolane guanine |
| ETV | entecavir |
| FAM | famciclovir |
| FCV | famciclovir |
| FTC | emtricitabine |
| HBIG | hepatitis B immunoglobulin |
| HBsAg | hepatitis B surface antigen |
| HBV | hepatitis B virus |
| LdT | beta-L thymidine |
| LMV | lamividuine |
| PMEA | 9-[phosphonyl-methoxyethyl]-adenine; adefovir |
| PMPA | 9-R-(2-phosphonomethoxypropyl)adenine |
| RNase | ribonuclease |
| rt ("rt" before "$Xaa_1nXaa_2$" means reverse transcriptase) | reverse transcriptase |
| s (as used in a mutation, e.g. sF134V) | envelope gene |
| TFV | tenofovir disoproxil fumarate |
| YMDD | Tyr Met Asp Asp-a motif in the polymerase protein; where the Met residue is designated residue number 204 of the reverse transcriptase |

BRIEF DESCRIPTION OF THE FIGURES

FIG. 4 is a representation showing comparison of the HBV nucleotide sequence (SEQ ID NO: 6) encoding the catalytic region of the polymerase gene in samples from Patient A.

FIG. 5 is a representation showing comparison of the deduced amino acid sequence SEQ ID NO: 7 of the catalytic region of the polymerase gene in samples from Patient A.

FIG. 6 is a representation showing comparison of the deduced amino acid sequence SEQ ID NO: 8 of the envelope gene in samples from Patient A.

FIG. 7 is a representation showing comparison of the HBV nucleotide sequence SEQ ID NO: 9 encoding the catalytic region of the polymerase gene in samples from Patient B FIG. 8 is a representation showing comparison of the deduced amino acid sequence SEQ ID NO: 10 of the catalytic region of the polymerase gene in samples from Patient B FIG. 9 is a representation showing comparison of the deduced amino acid sequence SEQ ID NO: 11 of the envelope gene in samples from Patient B.

FIG. 10 is a representation the HBV nucleotide sequence SEQ ID NO: 12 that also includes the encoding the catalytic region of the polymerase gene in samples from Patient C FIG. 11 is a representation the deduced amino acid sequence SEQ ID NO: 13 of the polymerase gene in samples from Patient C.

FIG. 12 is a representation the deduced amino acid sequence SEQ ID NO: 14 of the envelope gene in samples from Patient C.

FIG. 13 is a representation the HBV nucleotide sequence SEQ ID NO: 15 encoding the catalytic region of the polymerase gene in samples from Patient D.

FIG. 14 is a representation the deduced amino acid sequence SEQ ID NO: 16 of the catalytic region of the polymerase gene in samples from Patient D.

FIG. 15 is a representation the deduced amino acid sequence SEQ ID NO: 17 of the envelope gene in samples from Patient D.

FIG. 16 is a representation the HBV nucleotide sequence SEQ ID NO: 18 encoding the catalytic region of the polymerase gene in samples from Patient E.

FIG. 17 is a representation the deduced amino acid sequence SEQ ID NO: 19 of the catalytic region of the polymerase gene in samples from Patient E.

FIG. 18 is a representation the deduced amino acid sequence SEQ ID NO: 20 of the envelope gene in samples from Patient E.

FIG. 19 is a representation the HBV nucleotide sequence SEQ ID NO: 21 encoding the catalytic region of the polymerase gene in samples from Patient F.

FIG. 20 is a representation the deduced amino acid sequence SEQ ID NO: 22 of the catalytic region of the polymerase gene in samples from Patient F.

FIG. 21 is a representation the deduced amino acid sequence SEQ ID NO: 23 of the envelope gene in samples from Patient F.

FIG. 22 is a representation the HBV nucleotide sequence SEQ ID NO: 24 encoding the catalytic region of the polymerase gene in samples from Patient G.

FIG. 23 is a representation the deduced amino acid sequence SEQ ID NO: 25 of the catalytic region of the polymerase gene in samples from Patient G.

FIG. 24 is a representation the deduced amino acid sequence SEQ ID NO: 26 of the envelope gene in samples from Patient G.

FIG. 25 is a representation the HBV nucleotide sequence SEQ ID NO: 27 encoding the catalytic region of the polymerase gene in samples from Patient H.

FIG. 26 is a representation the deduced amino acid sequence SEQ ID NO: 28 of the catalytic region of the polymerase gene in samples from Patient H.

FIG. 27 is a representation the deduced amino acid sequence SEQ ID NO: 29 of the envelope gene in samples from Patient H.

FIG. 28 is a representation the HBV nucleotide sequence SEQ ID NO: 30 encoding the catalytic region of the polymerase gene in samples from Patient I.

FIG. 29 is a representation the deduced amino acid sequence SEQ ID NO: 31 of the catalytic region of the polymerase gene in samples from Patient I.

FIG. 30 is a representation the deduced amino acid sequence SEQ ID NO: 32 of the envelope gene in samples from Patient I.

DETAILED DESCRIPTION

Figure 1:
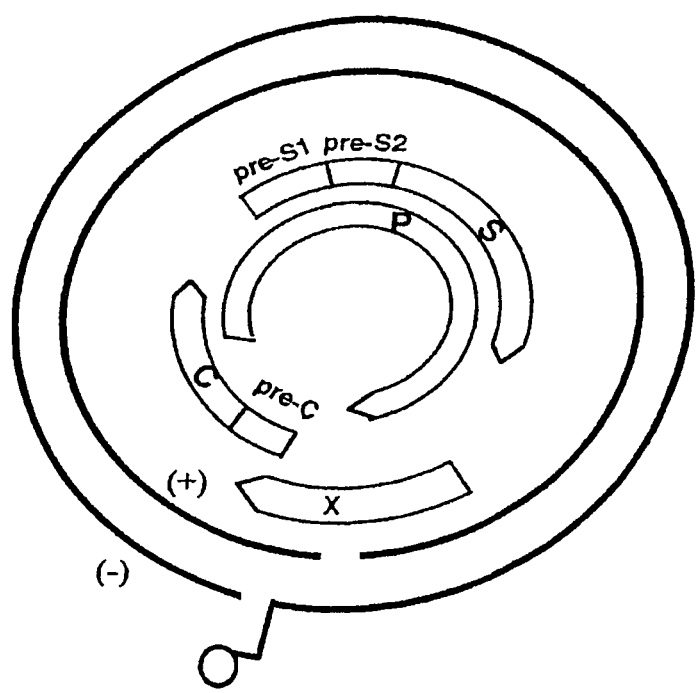
FIG. 1 is a diagrammatic representation showing the partially double stranded DNA HBV genome showing the overlapping open reading frames encoding surface (S), core (C), polymerase (P) and X gene.

The present invention is predicated in part on the identification and isolation of nucleoside or nucleotide analog-resistant variants of HBV following treatment of patients with either ADV or LMV or ETV or more particularly ADV and LMV or TFV and LMV, or ETV and optionally one or more other nucleoside analogs or nucleotide analogs or other anti-HBV agents such as TFV, LdT, or FTC. In particular, ADV or ADV and LMV or ETV treated patients gave rise to variants of HBV exhibiting decreased or reduced sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Reference herein to "decreased" or "reduced" in relation to sensitivity to ADV and/or LMV and/or FTC and/or TFV and/or ETV includes and encompasses a complete or substantial resistance to the nucleoside or nucleotide analog or other anti-HBV agents as well as partial resistance and includes a replication rate or replication efficiency which is more than a wild-type in the presence of a nucleoside or nucleotide analog or other anti-HBV agents. In one aspect, this is conveniently measured by an increase in viral load during treatment, or alternatively, there is no substantial decrease in HBV DNA viral load from pre-treatment HBV DNA levels during treatment (i.e., non-response to treatment).

Accordingly, one aspect contemplates an isolated Hepatitis B virus (HBV) variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Another aspect provides a method for determining the potential for an HBV to exhibit reduced sensitivity to a nucleoside or nucleotide analog selected from ADV, LMV, TFV, LdT, FTC and ETV or a combination thereof or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV, FTC and/or wherein the presence of such a mutation is an indication of the likelihood of resistance to said one or more of ADV, LMV, TFV, LdT, FTC and/or ETV.

A further aspect provides an isolated Hepatitis B virus (HBV) variant is provided wherein said variant comprises a nucleotide mutation in a gene encoding a DNA polymerase resulting in at least one amino acid addition, substitution and/or deletion to said DNA polymerase wherein the mutation is selected from the group consisting of:
(i) a mutation at codon 239, 240, 241, 242 and/or 243;
(ii) a mutation resulting in an N236I/D/V substitution;
(iii) a mutation resulting in an S246H/P/Y/S substitution;
(iv) a mutation resulting in a P170H substitution;
(v) a mutation resulting in an I253V substitution;
(vi) co-mutations of two or more substitutions selected from the list consisting of rtL42L/V, rtS78T, rtS85T, rtT128N, rtL180M, rtT184G, rtS202I, rtM204V and rtN236I/D/V;
(vii) co-mutations of two or more substitutions selected from the list consisting of rtF61L, rtS78T, rtV84M/V, rtV142E, rtQ149Q/R, rtM204I/M, rtI233T/I and rtS246H/P/Y/S; and
(viii) co-mutations of two or more substitutions selected from the list consisting of rtI29L, rtY50S, rtP170H, rtL180M, rtM204V and rtI253V;
wherein the HBV variant exhibits decreased sensitivity to a nucleoside or nucleotide analog.

Unless otherwise indicated, the present disclosure is not limited to specific formulations of components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms “a”, “an” and “the” include plural aspects unless the context clearly dictates otherwise. Thus, for example, reference to “a nucleoside or nucleotide analog” includes a single analog, as well as two or more analogs; reference to “an HBV variant” includes reference to two or more HBV variants; reference to “the invention” includes reference to a single or multiple aspect of the invention; and so forth.

The terms “analog”, “compound”, “active agent”, “pharmacologically active agent”, “medicament”, “active” and “drug” are used interchangeably herein to refer to a chemical compound that induces a desired effect such as inhibit viral replication, infection, maintenance, assembly and/or the function of an enzyme such as HBV DNA polymerase. The terms also encompass pharmaceutically acceptable and pharmacologically active ingredients of those active agents specifically mentioned herein including but not limited to salts, esters, amides, prodrugs, active metabolites, analogs and the like. When the terms “analog”, “compound”, “active agent”, “pharmacologically active agent”, “medicament”, “active” and “drug” are used, then it is to be understood that this includes the active agent per se as well as pharmaceutically acceptable, pharmacologically active salts, esters, amides, prodrugs, metabolites, analogs, etc.

Therefore, compounds are contemplated which are useful in inhibiting HBV replication, infection, maintenance, assembly and/or the function of an enzyme such as HBV DNA polymerase. Reference to an “analog”, “compound”, “active agent”, “pharmacologically active agent”, “medicament”, “active” and “drug” such as ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. A “combination” also includes a two-part or more such as a multi-part anti-HBV therapeutic composition where the agents are provided separately and given or dispensed separately or admixed together prior to dispensation.

The terms “effective amount” and “therapeutically effective amount” of an agent as used herein mean a sufficient amount of the agent to provide the desired therapeutic or physiological effect of inhibiting HBV replication, infection, maintenance, assembly and/or the function of an enzyme such as HBV DNA polymerase. Furthermore, an “effective HBV-inhibiting amount” or “effective symptom-ameliorating amount” of an agent is a sufficient amount of the agent to directly or indirectly inhibit replication, infection, maintenance, assembly and/or the function of an enzyme such as HBV DNA polymerase. Undesirable effects, e.g. side effects, are sometimes manifested along with the desired therapeutic effect; hence, a practitioner balances the potential benefits against the potential risks in determining what is an appropriate “effective amount”. The exact amount required will vary from subject to subject, depending on the species, age and general condition of the subject, mode of administration and the like. Thus, it may not be possible to specify an exact “effective amount”. However, an appropriate “effective amount” in any individual case may be determined by one of ordinary skill in the art using only routine experimentation.

By “pharmaceutically acceptable” carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a “pharmacologically acceptable” salt, ester, emide, prodrug or derivative of a compound as provided herein is a salt, ester, amide, prodrug or derivative that this not biologically or otherwise undesirable.

The terms “treating” and “treatment” as used herein refer to reduction in severity and/or frequency of symptoms, elimination of symptoms and/or underlying cause, prevention of the occurrence, of symptoms and/or their underlying cause, and improvement or remediation of damage in relation to HBV infection. Thus, for example, “treating” a patient involves prevention of HBV infection as well as treatment of a clinically HBV symptomatic individual by inhibiting HBV replication, infection, maintenance, assembly and/or the function of an enzyme such as HBV DNA polymerase. Thus, for example, the present method of “treating” a patient with HBV infection or with a propensity for one to develop encompasses both prevention of HBV infection as well as treating HBV infection or symptoms thereof. In any event, the present invention contemplates the treatment or prophylaxis of HBV infection.

“Patient” as used herein refers to an animal, preferably a mammal and more preferably a primate including a lower primate and even more preferably, a human who can benefit from the formulations and methods of the present invention. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an “animal” includes an avian species such as a poultry bird (including ducks, chicken, turkeys and geese), an aviary bird or game bird. The condition in a non-human animal may not be a naturally occurring HBV infection but HBV-like infection may be induced.

As indicated above, the preferred animals are humans, non-human primates such as marmossets, baboons, orangatangs, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

An "anti-HBV agent" includes a nucleoside or nucleotide analog, protein, chemical compound, RNA or DNA or RNAi or siRNA oligonucleotide (either DNA-derived or synthetic).

In a particular embodiment, the decreased sensitivity is in respect of ETV. Alternatively, the decreased sensitivity is in respect of ADV or LMV. Alternatively, the decreased sensitivity is in respect of TFV. Alternatively, the decreased sensitivity is in respect of FTC. Alternatively, the decreased sensitivity is in respect of ETV and optionally ADV and LMV. Alternatively, the decreased sensitivity is in respect of ADV and TFV and optionally ETV. Alternatively, the decreased sensitivity is in respect of LMV and TFV and optionally ETV. Alternatively, the decreased sensitivity is in respect of ADV and FTC and optionally ETV. Alternatively, the decreased sensitivity is in respect to FTC and TFV and optionally ETV. Alternatively, the decreased sensitivity is in respect of FTC and LMV and optionally ETV. Alternatively, the decreased sensitivity is in respect of ADV and LMV and TFV and optionally ETV. Alternatively, the decreased sensitivity is in respect to ADV and TFV and FTC and optionally ETV. Alternatively, the decreased sensitivity is in respect to LMV and TFV and FTC and optionally ETV. Alternatively, the decrease sensitivity is in respect of ADV and LMV and FTC and optionally ETV. Alternatively, the decreased sensitivity is in respect of ADV and FTC and TFV and LMV and optionally ETV.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release. Reference herein to "nucleic acid" includes reference to a sense or antisense molecule, RNA or DNA, oligonucleotides and RNAi and siRNA molecules and complexes containing same.

In addition to a mutation in the gene encoding DNA polymerase, due to the overlapping nature of the HBV genome (FIG. 1), a corresponding mutation may also occur in the gene encoding the S gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof or a reduced interactivity of an immunological reagent to HBsAg wherein the variant is selected for following ADV and/or LMV combination or sequential treatment. The term "sequential" in this respect means ADV followed by LMV and/or TFV and/or ETV, and/or FTC, LMV followed by ADV and/or TFV and/or FTC and/or ETV or ETV followed by one or more of ADV, FTC, LMV and/or TFV, or multiple sequential administrations of each of ETV, ADV, LMV and/or TFV and/or FTC.

A viral variant may, therefore, carry a mutation only in the DNA polymerase gene or both in the DNA polymerase gene and the S gene. The term "mutation" is to be read in its broadest context and includes multiple mutations.

A mutation in any domain of the HBV DNA polymerase and in particular regions F and G, and domains A through to E is contemplated herein provided the mutation leads to decreased sensitivity to ADV and/or LMV and/or TFV and/or ETV and/or FTC and/or LdT or combinations thereof.

In this specification, reference is particularly made to the conserved regions of the DNA polymerase as defined by domains A to E. Regions A to E are defined by the amino acid sequence set forth in Formula II in Australian Patent No. 734831.

Particularly, the mutation results in an altered amino acid sequence in any one or more of domains F and G, and domains A through to E or regions proximal thereto of the HBV DNA polymerase.

Another aspect provides an HBV variant comprising a mutation in an overlapping open reading frame in its genome wherein said mutation is in a region defined by one or more of domains F and G, and domains A through to E of HBV DNA polymerase and wherein said variant exhibits decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

A further aspect contemplates an HBV variant comprising a mutation in the nucleotide sequence encoding HBsAg resulting in an amino acid addition, substitution and/or deletion in said HBsAg wherein said variant exhibits decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

More particularly, a variant HBV is provided comprising a surface antigen having an amino acid sequence with a single or multiple amino acid substitution, addition and/or deletion or a truncation compared to a surface antigen from a reference or wild-type HBV and wherein an antibody generated to the reference or wild-type surface antigen exhibits reduced capacity for neutralizing said HBV variant, said variant selected by exposure of a subject to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

The term "combination therapy" means that both combinations of ADV, LMV, FTC, LdT, TFV, and/or ETV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of ADV, LMV, FTC, TFV, LdT or ETV and then completing a second or third or subsequent therapeutic courses with the other of ADV, LMV, FTC, TFV, LdT or ETV.

Accordingly, another aspect of contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV therapy or therapy by one or more other nucleoside or nucleotide analogs or other anti-HBV agents.

A further aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV therapy or therapy by one or more other nucleoside or nucleotide analogs or other anti-HBV agents.

Yet another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC therapy or therapy by one or more other nucleoside or nucleotide analogs or other anti-HBV agents.

Still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV therapy or therapy by one or more other nucleoside or nucleotide analogs or other anti-HBV agents.

Yet still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ETV therapy or therapy by one or more other nucleoside or nucleotide analogs or other anti-HBV agents.

Still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant BBV is selected for by exposure of a subject to LdT therapy or therapy by one or more other nucleoside or nucleotide analogs or other anti-HBV agents.

Even yet another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and LMV therapy or therapy by one or more other nucleoside or nucleotide analogs or other anti-HBV agents.

Even still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and TFV therapy or therapy by one or more other nucleoside or nucleotide analogs or other anti-HBV agents.

Yet still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and ETV therapy or therapy by one or more other nucleoside or nucleotide analogs or other anti-HBV agents.

A further aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and TFV therapy or therapy by one or more other nucleoside or nucleotide analogs or other anti-HBV agents.

Yet a further aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and ETV therapy or therapy by one or more other nucleoside or nucleotide analogs or other anti-HBV agents.

Another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and FTC therapy or therapy by one or more other nucleoside or nucleotide analogs or other anti-HBV agents.

Yet another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and FTC therapy or therapy by one or more other nucleoside or nucleotide analogs or other anti-HBV agents.

Still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and ETV therapy or therapy by one or more other nucleoside or nucleotide analogs or other anti-HBV agents.

Still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and LMV therapy or therapy by one or more other nucleoside or nucleotide analogs or other anti-HBV agents.

Even another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and ETV therapy or therapy by one or more other nucleoside or nucleotide analogs or other anti-HBV agents.

Even yet another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV and/or ETV therapy or therapy by one or more other nucleoside or nucleotide analogs or other anti-HBV agents.

Even still another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV and/or ETV therapy or therapy by one or more other nucleoside or nucleotide analogs or other anti-HBV agents.

A further aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and FTC and/or ETV therapy or therapy by one or more other nucleoside or nucleotide analogs or other anti-HBV agents.

Another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC, LMV and TFV and/or ETV therapy or therapy by one or more other nucleoside or nucleotide analogs or other anti-HBV agents.

Yet another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, FTC and TFV and/or ETV therapy or therapy by one or more other nucleoside or nucleotide analogs or other anti-HBV agents.

Still yet another aspect contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV, FTC and TFV and/or ETV therapy or therapy by one or more other nucleoside or nucleotide analogs or other anti-HBV agents.

Particularly, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs such as but not limited to an isolated HBsAg. Accordingly, the present invention provides an isolated HBsAg or a recombinant form thereof or derivative or chemical equivalent thereof, said HBsAg being from a variant HBV selected by exposure of a subject to one or more of ADV, LMV, FTC, TFV and/or ETV or optionally one or more nucleoside or nucleotide analogs or other anti-HBV agents.

More particularly, an isolated variant HBsAg or a recombinant or derivative form thereof or a chemical equivalent thereof is provided wherein said HBsAg or its recombinant or derivative form or its chemical equivalent exhibits an altered immunological profile compared to an HBsAg from a reference HBV, said HBsAg being from a variant HBV selected by exposure of a subject to one or more of ADV, LMV, FTC, TFV and/or ETV or optionally one or more nucleoside or nucleotide analogs or other anti-HBV agents.

Even more particularly, an isolated variant HBsAg or a recombinant or derivative form thereof or a chemical equivalent thereof is provided wherein said HBsAg or its recombinant or derivative form or its chemical equivalent comprises an amino acid sequence with a single or multiple amino acid substitution, addition and/or deletion or a truncation compared to an HBsAg from a reference HBV and wherein a neutralizing antibody directed to a reference HBV exhibits no or reduced neutralising activity to an HBV carrying said variant HBsAg, said HBsAg being from a variant HBV selected by exposure of a subject to one or more of ADV, LMV, FTC, TFV and/or ETV or optionally one or more nucleoside or nucleotide analogs or other anti-HBV agents.

Particular mutations in the HBV DNA polymerase include variants selected from patients with HBV recurrence following ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Nucleoside or nucleotide analogs or other anti-HBV agents may be indicated during, after or prior to a transplantation procedure (e.g. bone marrow transplantation (BMT) or OLT) or following treatment of patients diagnosed with hepatitis. Following selection of variants, viral loads are obtainable at levels similar to pre-treatment levels or increase while on therapy.

Useful mutants in the rt region include, in one embodiment includes, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent mutation.

Particularly useful mutants are co-mutations at codons 180, 184 and 204 such as rtL180M and rtT184S and rtM204V, or co-mutations at codons 85, 180, 184, 202, 204 and 236 such as rtS85T, rtL180M, rtT184G, rtS202I, rtM204V and rtN236I/DN. Alternative useful mutations contemplated herein include rtP170H, rtT184A, rtY221H/Y, rtI233T/I, rtT240N/T, rtK241R, rtR242K/R, rtW243R/W, rtI253V, rtI254I/F, rtS256R/S rtW257G/W, rtY257H or mutations at codon 239. A "co-mutation" means that a variant will comprise mutations at all mentioned codons. The present invention is particularly directed to co-mutations at codons 180, 184 and 204 as well as co-mutations at codons 85, 180, 184, 202, 204 and 236 but does not extend to a double mutation at codons 180 and 204 alone.

Such HBV variants are proposed to exhibit a decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof. It should be noted that the nomenclature system for amino acid positions is based on the methionine residues in the YMDD motif being designated codon rtM204. This numbering system is different to that in Australian Patent No. 734831 where the methionine residue in the YMDD motif within the polymerase gene is designated codon 550. In this regard, rtL180M and rtM204V correspond to L526M and M550V, respectively, in Australian Patent No. 734831. Corresponding mutations may also occur in envelope genes such as in one or more of PreS1, PreS2 and S.

Another potential mode of action of ADV and other acyclic nucleoside phosphonates is that of immune stimulation (Calio et al, *Antiviral Res.* 23:77-89, 1994). A number of mutations resulted in changes in the envelope gene detected in HBV variants which may be associated with immune escape. These changes include in one embodiment include sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or a combination thereof or an equivalent mutation.

Particularly useful mutants are sI110V, sP120Q, sF134L/F, sL162I, sL173F, sL175F, sL176V and sP178P/L.

The identification of the variants herein permits the generation of a range of assays to detect such variants. The detection of such variants may be important in identifying resistant variants to determine the appropriate form of chemotherapy and/or to monitor vaccination protocols, or develop new or modified vaccine preparations.

Still another aspect contemplates a method for determining the potential for an HBV to exhibit reduced sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and A domains through to E or a region proximal thereto of said DNA polymerase and associated with resistance or decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents wherein the presence of such a mutation is an indication of the likelihood of resistance to said ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents.

Accordingly, another aspect provides a method for determining the potential for an HBV to exhibit reduced sensitivity to a nucleoside or nucleotide analog selected from ADV, LMV, TFV, LdT, FTC and ETV or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV, LdT, FTC and/or ETV wherein the presence of such a mutation is an indication of the likelihood of resistance to said one or more of ADV, LMV, TFV, LdT, FTC and/or ETV.

Particularly, the assay detects one or more of the following mutations: in one embodiment includes, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent mutation is indicative of a variant wherein said variant exhibits a decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof.

Accordingly, another aspect produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment include sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or a combination thereof or an equivalent mutation, in even still another embodiment one embodiment includes, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM2041/M, rtI233T/I and rtS246H/P/Y/S, or finally in another embodiment includes rtI29L, rtY50S, rtP170H, rtL180M, rtM204V and rtI253V, or combinations thereof or an equivalent one or more other mutation is indicative of a variant which exhibits a decreased sensitivity to ADV, LMV, TFV, LdT, ETV or FTC; ADV and LMV; ADV and TFV; LMV and TFV; FTC and ADV; FTC and TFV;

FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

A further aspect produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment include s192T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or a combination thereof or an equivalent mutation, in even still another embodiment, in one embodiment includes, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or combinations thereof or an equivalent one or more other mutation is indicative of a variant which exhibits a decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplicon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Another aspect contemplated herein provides a method for detecting a variant HBV exhibiting an altered immunological profile said method comprising isolating an HBV from a subject exposed to a nucleoside or nucleotide analog selected from the listed consisting of ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting said HBV with a panel of one or more antibodies to a surface antigen and screening for any change in binding affinity or binding spectrum.

In a related embodiment, a method is contemplated for detecting a variant HBV exhibiting an altered immunological profile said method comprising isolating a serum sample from a subject exposed to a nucleoside or nucleotide analog selected from the listed consisting of ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum.

Detecting HBV replication in cell culture is particularly useful.

This and other aspects are particularly amenable to microarray analysis such as to identify oligonucleotides including sense and antisense molecules, RNAi or siRNA molecules or DNA or RNA-binding molecules which down-regulate genomic sequences or transcripts of HBV. Microarray analysis may also be used to identify particular mutations in the HBV genome such as within the HBV DNA polymerase-coding region or the HBsAg-coding region.

Another aspect of contemplates a method for detecting an agent which exhibits inhibitory activity to an HBV by:
generating a genetic construct comprising a replication competent-effective amount of the genome from the HBV contained in a plasmid vector and then transfecting said cells with said construct;
contacting the cells, before, during and/or after transfection, with the agent to be tested;
culturing the cells for a time and under conditions sufficient for the HBV to replicate, express genetic sequences and/or assemble and/or release virus or virus-like particles if resistant to said agents; and
then subjecting the cells, cell lysates or culture supernatant fluid to viral- or viral-component-detection means to determine whether or not the virus has replicated, expressed genetic material and/or assembled and/or been released in the presence of the agent.

In a particular embodiment, the plasmid vector may include genes encoding part or all of other viral vectors such as baculovirus or adenovirus (Ren and Nassal, 2001, supra) and the method comprises:
generating a genetic construct comprising a replication competent-effective amount of the genome from the HBV contained in or fused to an amount of a baculovirus genome or adenovirus genome effective to infect cells and then infecting said cells with said construct;
contacting the cells, before, during and/or after infection, with the agent to be tested;
culturing the cells for a time and under conditions sufficient for the HBV to replicate, express genetic sequences and/or assemble and/or release virus or virus-like particles if resistant to said agent; and
then subjecting the Cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:
generating a continuous cell line comprising an infectious copy of the genome of the HBV in a replication competent effective amount such that said infectious HBV genome is stably integrated into said continuous cell line such as but not limited to 2.2.15 or AD;
contacting the cells with the agent to be tested;
culturing the cells for a time and under conditions sufficient for the HBV to replicate, express genetic sequences and/or assemble and/or release virus or virus-like particles if resistant to the agent; and
then subjecting the cells, cell lysates or culture supernatant fluid to viral- or viral-component-detection means to determine whether or not the virus has replicated, expressed genetic material and/or assembled and/or been released in the presence of the agent.

The above-mentioned methods are particularly useful in identifying or developing agents against HBV variants such as those carrying mutations, in one embodiment includes rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent mutation; in a further embodiment includes sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or a combination thereof or an equivalent mutation.

Accordingly, another aspect contemplates a method for determining whether an HBV strain exhibits reduced sensitivity to a nucleoside or nucleotide analog or other potential anti-HBV agent, said method comprising isolating DNA or corresponding mRNA from said HBV and screening for a mutation in the nucleotide sequence of the envelope genes or DNA polymerase gene selected from, in one embodiment includes, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent mutation; in a further embodiment, in one embodiment include sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY2251I/Y, and finally in another embodiment includes sL20F, sI42L, sV144D, sL162I and sI195M or a combination thereof or an equivalent mutation and/or optionally other nucleoside or nucleotide analogs or other anti-HBV agents or combination thereof.

The detection of amino acid variants of DNA polymerase is conveniently accomplished by a range of amino acid detection techniques. Where an HBV variant comprises an amino acid change, then such an isolate is considered a putative HBV variant having an altered DNA polymerase activity.

Further contemplated herein are agents which inhibit ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof resistant HBV variants. Such agents are particularly useful if long term treatment by ADV, LMV, FTC, TFV, LdT and/or ETV and/or optionally other nucleoside or nucleotide analogs such as TFV is contemplated by the clinician. The agents may be DNA or RNA or proteinaceous or non-proteinaceous chemical molecules. Natural product screening such as from plants, coral and microorganisms is also contemplated as a useful potential source of masking agents as is the screening of combinatorial or chemical libraries. The agents may be in isolated form or in the form of a pharmaceutical composition or formulation and may be administered in place of or sequentially or simultaneously with a nucleoside or nucleotide analog. Furthermore, rationale drug design is contemplated including solving the crystal or NMR structure of, for example, HBV DNA polymerase and designing agents which can bind to the enzyme's active site. This approach may also be adapted to other HBV components.

Accordingly, another aspect contemplates a method for detecting an agent which exhibits inhibitory activity to an HBV which exhibits resistance or decreased sensitivity ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Still another aspect provides a method for detecting an agent which exhibits inhibitory activity to an HBV which exhibits resistance or decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Particularly, the HBV genome is stably integrated into the cells' genome.

Useful cells include 2.2.15 cells (Price et al, *Proc. Natl. Acad. Sci. USA* 86(21):8541-8544, 1989 or AD cells (also known as HepAD32 cells or HepAD79 cells [Ying et al, 2000, supra].

Whilst the baculovirus vector is a particularly useful in the practice of the instant method a range of other vectors may also be used such as but not limited to adenoviral vectors.

Cell lines (e.g. 2.2.15 or AD cells) carrying genetic constructs comprising all or a portion of an HBV genome or a gene or part of a gene therefrom are also contemplated herein.

Also provided is the use of the subject HBV variants to screen for anti-viral agents. These anti-viral agents inhibit the virus. The term "inhibit" includes antagonizing or otherwise preventing infection, replication, assembly and/or release or any intermediate step. Particular anti-viral agents include nucleoside or nucleotide analogs or anti-HBV agents, as well as non-nucleoside molecules.

In addition, rational drug design is also contemplated to identify or generate chemical molecules which either mimic a nucleoside or which interact with a particular nucleotide sequence or a particular nucleotide. Combinatorial chemistry and two hybrid screening are some of a number of techniques which can be employed to identify potential therapeutic or diagnostic agents.

In one example, the crystal structure or the NMR structure of polymerase or the surface antigen is used to rationally design small chemical molecules likely to interact with key regions of the molecule required for function and/or antigenicity. Such agents may be useful as inhibitors of polymerase activity and/or may alter an epitope on the surface antigen.

Several models of the HBV polymerase have been prepared due to the similarity with reverse transcriptase from HIV (Das et al, *J. Virol.* 75(10:4771-4779, 2001; Bartholomeusz et al, *Intervirology* 40(5-6):337-342 1997; Allen et al, *Hepatology* 27(6):1670-1677, 1998). The models of the HBV polymerase can be used for the rational drug design of new agents effective against HBV encoding the resistant mutations as well as wild type virus. The rational drug that is designed may be based on a modification of an existing antiviral agent such as the agent used in the selection of the HBV encoding the mutations associated with resistance. Viruses or clones expressing HBV genomic material encoding the mutations may also be used to screen for new antiviral agents.

In an alternative embodiment, a method is contemplated for detecting an agent which exhibits inhibitory activity to an HBV polymerase in an in vitro polymerase assay. The HBV polymerase activity can be examined using established assays (Gaillard et al, 2002, supra; Xiong et al, 1998, supra).

As indicated above, microarray technology is also a useful means of identifying agents which are capable of interacting with defined HBV internal or external components. For example, arrays of HBV DNA polymerase or peptide fragments thereof carrying different amino acid variants may be used to screen for agents which are capable of binding or otherwise interacting with these molecules. This is a convenient way of determining the differential binding patterns of agents between HBV variants. Arrays of antibodies may also be used to screen for altered HBsAg molecules. Microarrays are also useful in proteomic analysis to identify molecules such as antibodies, interferons or cytokines which have an ability to interact with an HBV component. Microarrays of DNA and RNA molecules may also be employed to identify sense and antisense molecules for genetic regions on the HBV genome or transcripts thereof.

The above methods are particularly useful in identifying an inhibitor of an HBV resistant to or exhibiting reduced sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof. The present invention extends, therefore, to compositions of the inhibitors. The inhibitors may also be in the form of antibodies or genetic molecules such as ribozymes, antisense molecules and/or sense molecules for co-suppression or the induction of RNAi or may be other nucleoside or nucleotide analogs or other anti-HBV agents or derivatives of known analogs. Reference to RNAi includes reference to short, interfering RNAs (siRNA) and all RNAi-type molecules may be DNA-derived or synthetic.

The term "composition" includes a "pharmaceutical composition" or a formulation.

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavouring. Of course, any material used in preparing any dosage unit form should be pharmaceutically pure and substantially non-toxic in the amounts employed. In addition, the active compound(s) may be incorporated into sustained-release preparations and formulations.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Yet another aspect provides a composition comprising a variant HBV resistant to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or an HBV surface antigen from said variant HBV or a recombinant or derivative form thereof or its chemical equivalent and one or more pharmaceutically acceptable carriers and/or diluents. Such a composition may be regarded as a therapeutic composition and is useful in generating an immune response including a humoral response. Generally, the HBV variants are "defective" and in themselves are unable to cause a sustained infection in a subject.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complimentarity determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC II complex.

Insofar as ribozyme, antisense or co-suppression (RNAi) or siRNA or complexes thereof repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

In another embodiment, provided is a biological composition comprising a variant HBV or an HBsAg or L, M or S proteins from said variant HBV or a recombinant or derivative form thereof or its chemical equivalent.

Generally, if an HBV is used, it is first attenuated. The biological composition generally further comprises one or more pharmaceutically acceptable carriers and/or diluents.

The biological composition may comprise HBsAg or like molecule from one HBV variant or the composition may be a cocktail of HbsAgs or L, M or S proteins or like molecules from a range of ADV- and/or LMV- and/or, FTC-LdT-, and/or TFV-resistant HBV variants. Similar inclusions apply where the composition comprises an HBV.

Further provided is the use of defective HBV variants in the manufacture of therapeutic vaccines to vaccinate individuals against infection by HBV strains having a particular nucleotide sequence or encoding a particular polymerase or surface antigen or L, M or S proteins.

Examples of suitable vaccine candidates are defective forms of HBV variants comprising a mutation selected from, in one embodiment includes, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84M/V, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent mutation; in a further embodiment, sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or a combination thereof or an equivalent mutation.

In one embodiment, for example, an HBV variant may be identified having a particular mutation in its polymerase conferring resistance or decreased sensitivity to a nucleoside or nucleotide analog. This variant may then be mutated to render it defective, i.e. attenuated or unable to cause infection. Such a defective, nucleoside or nucleotide analog-resistant virus may then be used as a therapeutic vaccine against virulent viruses having the same mutation in its polymerase.

The subject invention extends to kits for assays for variant HBV resistant to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of contemplates a method for determining the potential for an HBV to exhibit reduced sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and domains A through to E or a region proximal thereto of said DNA polymerase and associated with resistance or decreased sensitivity to ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, wherein the presence of such a mutation is an indication of the likelihood of resistance to said ADV, LMV, TFV, LdT, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

An assessment of a potential viral variant is important for selection of an appropriate therapeutic protocol. Such an assessment is suitably facilitated with the assistance of a computer programmed with software, which inter alia adds input codes for at least two features associated with the viral variants to provide a value corresponding to the resistance or sensitivity of a viral variant to a particular chemical compound or immunological agent. The value can be selected from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, the values for such features are stored in a machine-readable storage medium, which is capable of processing the data to provide a value for a particular viral variant or a biological specimen comprising same.

Thus, in another aspect, a computer program product is contemplated for assessing the likely usefulness of a viral variant or biological sample comprising same for determining an appropriate therapeutic protocol in a subject (FIG. 15), said product comprising:
  (1) code that receives as input code for at least two features associated with said viral agents or biological sample comprising same, wherein said features are selected from:
    (a) the ability to exhibit resistance for reduced sensitivity to a particular compound or immunological agent;
    (b) an altered DNA polymerase from wild-type HBV;
    (c) an altered surface antigen from wild-type HBV; or
    (d) morbidity or recovery potential of a patient;
  (2) code that adds said input code to provide a sum corresponding to a value for said viral variants or biological samples; and
  (3) a computer readable medium that stores the codes.

In a related aspect, a computer is provided for assessing the likely usefulness of a viral variant or biological sample comprising same in a subject, wherein said computer comprises:
  (1) a machine-readable data storage medium comprising a data storage material encoded with machine-readable data, wherein said machine-readable data comprise input codes for at least two features associated with said viral variant or biological sample; wherein said features are selected from:—
    (a) the ability to exhibit resistance for reduced sensitivity to a particular compound or immunological agent;
    (b) an altered DNA polymerase from wild-type HBV;
    (c) an altered surface antigen from wild-type HBV; or
    (d) morbidity or recovery potential of a patient;
  (2) a working memory for storing instructions for processing said machine-readable data;
  (3) a central-processing unit coupled to said working memory and to said machine-readable data storage medium, for processing said machine readable data to provide a sum of said input code corresponding to a value for said compound(s); and (4) an output hardware coupled to said central processing unit, for receiving said value.

Any general or special purpose computer system is contemplated by the present invention and includes a processor in electrical communication with both a memory and at least one input/output device, such as a terminal. FIG. 15 shows a generally suitable computer system. Such a system may include, but is not limited, to personal computers, workstations or mainframes. The processor may be a general purpose processor or microprocessor or a specialized processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network.

In an alternative embodiment, the program screens for a mutation selected from, in one embodiment, rtS256R/S and rtW257G/W, in another embodiment includes rtH9D, rtL180M, rtM204V, rtT184S and rtN238T, or yet another embodiment includes rtQ215S, rtR242K/R, and rtW243R/W, or yet another embodiment includes rtN118S, rtR120R, rtT184A and rtY257H, or still another embodiment includes rtH216H/P, rtL229M/L, rtI233T/I, rtT240N/T, rtK241R and rtH248N or yet another embodiment includes rtL180M, rtA181V, rtM207V, rtH216H/P, rtE218D/E, rtH238D, rtR242K/R, rtW243G/W and rtI254I/F, or still another embodiment includes rtY221H/Y, rtV214A, rtA181A/V and rtN236T, or still another embodiment includes rtL42L/V, rtS78T, rtS85T, rtT128N, rtL180M, rtT184G, rtS202I, rtM204V and rtN236I/D/V, or yet another embodiment includes rtF61L, rtS78T, rtV84MN, rtV142E, rtQ149Q/R, rtM204I/M, rtI233T/I and rtS246H/P/Y/S, or finally in another embodiment includes rtI29L, rtY50S, rtP170H, rtL180M, rtM204V and rtI253V, or a combination thereof or an equivalent mutation; in a further embodiment sI92T/I, sL175F and sI195M, in another embodiment include sS207R, or yet another embodiment include sI110V and sP120Q, or yet another embodiment include sF80S, sI208I/L, sS210K, sF220L/F and sY225H/Y, or yet another embodiment includes sF134L/F and sL173F, or yet another embodiment includes sC76Y and sL173F, or yet another embodiment includes sD33D/E, sC69 Stop, sC76 Stop, sR79H, sP120T, sL176V, sV194F and sI195M, or yet another embodiment includes sC69Stop, sM75I/M, sY134N, sK141K/E, sP178P/L, sW196stop/W, s210R/S and sY225H/Y, and finally in another embodiment includes sL20F, sI42L, sV144D, sL162I and sI195M or a combination thereof or an equivalent mutation.

The present invention is further described by the following non-limiting Examples.

EXAMPLE 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large proteins HBV surface antigens. The large protein component is referred to as the HBV surface antigen (HBsAg) and is encoded by the S gene sequence. The Pre-S1 and Pre-S2 gene sequences encode the other envelope components.

EXAMPLE 2

Patients on TFV and LMV and Analysis of HBV DNA

Patient A: During TFV and LMV treatment, unique HBV mutations were detected by sequencing (Table 4). This patent has had selected unique mutations at rtS256R/S and rtW257G/W (Table 4, FIGS. 4, 5, and 6) during virological breakthrough on treatment. These changes do not alter the HBsAg in the overlapping reading frame as they are after the termination codon in the HBsAg reading frame.

Patient B: During TFV and LMV treatment, unique HBV mutations were detected by sequencing (Table 5 and FIGS. 7, 8, and 9). The unique changes in the rt region of the HBV DNA polymerase include rtL180M+rtM204V previously demonstrated to be associated with LMV resistance inconjunction with a mutation at codon 184 (rtT184S) and rtH9D and rtN238T. The change at codon 184 in the rt has been previously noted with ETV+/−LMV resistance (Tenney et al, *Antimicrob Agents Chemother* 48(9):3498-507, 2004) but has not been reported with TFV+LMV resistance and virological breakthrough during treatment.

The changes in the HBsAg while on TFV and LMV treatment include sI92T/I, sL175F and sI195M. The last two changes correspond to changes in the polymerase at rtT184S and rtM204V, respectively.

Patient C: The HBV mutations during LMV and TFV treatment are listed in Table 6 and FIGS. 10, 11, 12. The unique changes in the rt region of the HBV DNA polymerase include rtR242K/R, W243R/W and rtQ215S. The changes in the HBsAg while on LMV and TFV treatment include sS207R.

Patient D: The HBV mutations during LMV and TFV treatment are listed in Table 7 and FIGS. 13, 14, 15. The unique changes in the rt region of the HBV DNA polymerase include rtT184A and rtY257H other changes include rtN118S and rtR102E.

The changes in the HBsAg while on LMV and TFV treatment include sI110V and sP120Q.

EXAMPLE 3

Patients on Antiviral Therapy and Analysis of HBV DNA

Treatment of patients with chronic hepatitis B virus with nucleos(t)ide analogs can result in the selection of HBV variants encoding mutations that may be associated with reduced sensitivity to the antiviral agent.

Resistance to ADV has been associated with a mutations in the putative tri-phosphate binding site at rtN236T (Angus et al, *Gastroenterolog.* 125(2):292-297, 2003). Therefore other mutations in this region selected by ADV or other antiviral treatments may be important in antiviral resistance against ADV and/or other nucleos(t)ide treatments. Important codons include 239 which is highly conserved, 240, 241, 242 and 243.

In addition to the mutation at rtN236T, other mutations may increase resistance and/or replication. Once such mutation is at codon 221

Patient E: The HBV mutations during LMV treatment are listed in Table 8 and FIGS. 16, 17, and 18. The unique changes in the rt region of the HBV DNA polymerase include rtT240N/T and rtK241R. Other important unique changes include rtH216H/P, rtL229M/L, rtI233T.

The changes in the HBsAg while on LMV treatment include sF80S, sI208UL, sS210K, sF220L/F and sY225H/Y.

Patient F: The HBV mutations during LMV treatment are listed in Table 9 and FIGS. 19, 20, and 21. The unique changes in the rt region of the HBV DNA polymerase include, rtR242R/K and rtW243G/W. Other important unique changes include rtL180M, rtA181T, rtH216H/P and rtE218D/E, refer to Table 9 for all other changes.

The important changes in the HBsAg in or near the "a" determinant while on LMV treatment include sF134L/F and sL173F (refer to Table 9 for all other changes).

Patient G: The HBV mutations during LMV treatment are listed in Table 10 and FIGS. 22, 23 and 24. The unique changes in the rt region of the HBV DNA polymerase include rtY221H/Y. Other important unique changes include rtV214A, rtA181A/V and rtN236T. (Refer to Table 9 for all other changes).

The important changes in the HBsAg in or near the "a" determinant while on LMV treatment include sL173F (refer to Table 9 for all other changes).

Patient H.

Patient H has been previously treated with a number of nucleoside/nucleotide analogs and was resistant individually to LMV, then ETV, then ADV. The patient was subsequently treated with combination LMV and ADV and ETV and is now resistant to all these agents. The HBV mutations during treatment are listed in FIGS. 25, 26 and 27.

This patient has selected unique combinations of mutations rtL42L/V, rtS78T, rtS85T, rtT128N, rtL180M, rtT184G, rtS202I, rtM204V, and rtN236I/D/V.

This includes the known LMV resistant mutations at rtL180M and rtM204V also the known ETV resistant mutations at rtL180M, rtT184G, rtS202I, and rtM204V. This patient has selected unique mutations at codon 236 at rtN236I/D/V that have not previously been reported with ADV resistance. Together all these mutations may be important for the combined ADV, LMV and ETV resistance mutations.

Changes in the HBsAg include sD33D/E, sC69 Stop, sC76 Stop, sR79H, sP120T, sL176V, sV194F and sI195M.

Patient I

Patient I was previously treated with LMV, then ADV. This patient is now being treated with TFV and LMV and has selected mutations which may be associated with reduced sensitivity to these agents. The HBV mutations during TDF and LMV treatment are listed in FIGS. 28, 29 and 30.

This includes the mutations at rtF61L, rtS78T, rtV84M/V, rtV142E, rtQ149Q/R, rtM204I/M, rtI233T/I and rtS246H/P/Y/S. In particular the mutation at rtI233T/I was not detected previously in HBV isolated from this patient pre-TFV treatment.

Changes in the HBsAg include sC69Stop, sM75I/M, sY134N, sK141K/E, sP178P/L, sW196stop/W, s210R/S, and sY225H/Y.

Patient J

Patient J was previously treated with LMV and selected HBV with mutations associated with LMV resistance this includes the polymerase mutations at rtI29L, rtY50S, rtP170H, rtL180M, rtM204V and rtI253V and the envelope mutations at sL20F, sI42L, sV144D, sL162I and sI195M.

This patient was subsequently treated with ADV and did not respond and then ETV and also did not respond. This suggests that this patient may have selected mutations during LMV treatment that may have affected the subsequent antiviral non-response or primary resistance to ADV and then ETV.

In particular the mutations at rtI253V and rtP170H may be important for the primary resistance to ADV and ETV.

EXAMPLE 4

Detection of Viral Markers

Hepatitis B surface antigen (HBsAg), hepatitis B e antigen (HBeAg), anti-HBe and hepatitis B core antigen (HBcAg) specific IgG and IgM were measured using commercially available immunoassays (Abbott Laboratories, North Chicago, Ill., USA). Hepatitis B viral DNA levels were measured using a capture hybridization assay according to the manufacturer's directions (Digene Hybrid Capture II, Digene Diagnostics Inc., Beltsville, Md.). The manufacturers stated cut-off for detecting HBV viremia in clinical specimens was $0.7 \times 10^6$ copies/ml or 2.5 pg/ml, [Hendricks et al, *Am J Clin Pathol* 104:537-46, 1995]. HBV DNA levels can also be quantitated using other commercial kits such as Cobas amplification HBV monitor kit (Roche).

EXAMPLE 5

Sequencing of HBV DNA

HBV DNA was extracted from 100 µl of serum as described previously by Aye et al, *J. Hepatol.* 26:1148-1153, 1997. Oligonucleotides were synthesized by Geneworks, Adelaide, Australia. Amplification of the HBV polymerase gene has been described by Aye et al, 1997, supra.

The specific amplified products were purified using PCR purification columns from MO BIO Laboratories Inc (La Jolla, Calif.) and directly sequenced using Big Dye terminator Cycle sequencing Ready Reaction Kit (Perkin Elmer, Cetus Norwalk, Conn.). The PCR primers were used as sequencing primers, OS1 5'-GCC TCA TTT TGT GGG TCA CCA TA-3' (nt 1408-1430) [SEQ ID NO:1], TTA3 5'-AAA TTC GCA GTC CCC AAA-3' (nt2128-2145) [SEQ ID NO:2], JM 5'-TTG GGG TGG AGC CCT CAG GCT-3' (nt1676-1696) [SEQ ID NO:3], TTA4 5'-GAA AAT TGG TAA CAG CGG-3' (nt 2615-2632) [SEQ ID NO:4], OS2 5' TCT CTG ACA TAC TTT CCA AT 3' (nt 2798-2817) [SEQ ID NO:5], to sequence the internal regions of the PCR products.

EXAMPLE 6

Adefovir Dipivoxil

ADV

Figure 2:
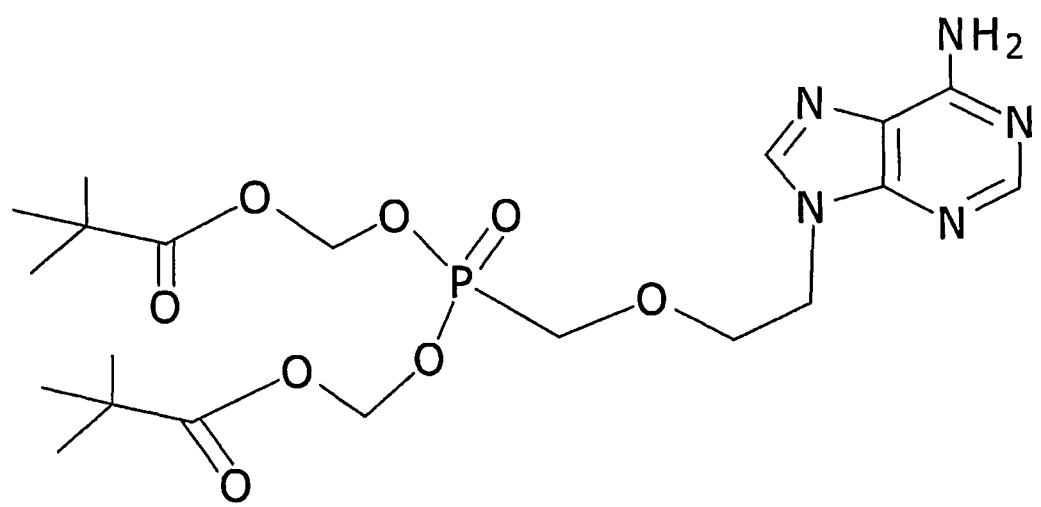
FIG. 2 is a diagrammatic representation of the chemical structure of ADV.
Figure 3:
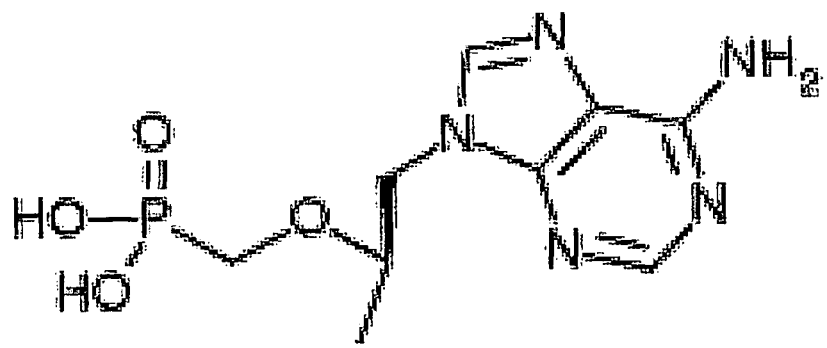
FIG. 3 is a diagrammatic representation of the chemical structure of Tenofovir.

ADV (formerly Bis-pom PMEA)) is a potent inhibitor of HBV replication. The structure of ADV is shown in FIG. 2 and its synthesis is described by Benzaria et al, *J Med Chem.* 39:4958-4965, 1996.

EXAMPLE 7

Tenofovir

TFV

TFV (formerly Bis-pom PMPA) is a potent inhibitor of HBV replication. The structure of tenofovir is shown in FIG.

3 and its synthesis is described by Srinivas and Fridland, *Antimicrob Agents Chemother.* 42(6):1484-1487, 1998.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 4

Patient A HBV Polymerase and envelope mutations detected duringTFV/LMV therapy

| Viral Load (IU/ml) | ALT (IU/ml) | G'type | Polymerase # |
|---|---|---|---|
|  | 114 | A | wildtype |
|  | 25 | PCR-ve |  |
|  | 24 | PCR-ve |  |
| 1.79E+07 |  | A | S256R/S W257G/w |

TABLE 5

Patient B HBV Polymerase and envelope mutations detected duringTFV/LMV therapy

| Viral Load (IU/ml) | ALT (IU/ml) | G'type | Polymerase # | HBsAG# |
|---|---|---|---|---|
|  |  | C | H9D L180M T184S M204V | I92T/I L175F I195M |
| 1.99E+07 |  | C | H9D L180M T184S M204V N238T | I92T/I L175F I195M |
| 1.06E+06 |  | C | H9D L180M T184S M204V N238N/T | I92T/I L175F I195M |
| 1.42E+05 |  | C | H9D L180M T184S M204/V | I92T/I L175F I195I/M |
| 1.00E+08 |  | C | H9D L180M T184S M204V N238T | I92T/I L175F I195M |

TABLE 6

Patient C HBV Polymerase and envelope mutations detected duringTFV/LMV therapy

| Viral Load (IU/ml) | ALT (IU/ml) | G'type | Polymerase # | HBsAG# |
|---|---|---|---|---|
| 1.70E+09 | 71 | D | V191I/V Q215P/S | W182*/W S207R |
|  | 55 | D | V191I/V Q215P/S | W182*/W S207R |
| 2.82E+05 |  | D | Q215S R242K/R W243R/W | S207R |

TABLE 7

Patient D HBV Polymerase and envelope mutations detected during TFV and LMV therapy

| Viral Load (IU/ml) | ALT (IU/ml) | G'type | Polymerase # | HBsAG# |
|---|---|---|---|---|
|  |  | D | N118S R120R T184A Y257H | I110V P120Q |

TABLE 8

Patient E HBV Polymerase and envelope mutations detected during LMV therapy

| Viral Load (IU/ml) | ALT (IU/ml) | G'type | Polymerase # | HBsAG# |
|---|---|---|---|---|
|  |  | D | F122V/F S135Y H216H/P L229M/L I233T/I T240N/T K241R | F80S I208I/L S210K F220L/F Y225H/Y |

TABLE 9

Patient F HBV Polymerase and envelope mutations detected during LMV therapy

| Viral Load (IU/ml) | ALT (IU/ml) | G'type | Polymerase # | HBsAG# |
|---|---|---|---|---|
|  |  | B | N124D S135A S143T/S L180M A181V H216H/P E218D/E H238D R242K/R W243G/W I254I/f | F134L/F L173F I208I/L S210T/S |

TABLE 10

Patient G HBV Polymerase and envelope mutations detected during ADV therapy

| Viral Load (IU/ml) | ALT (IU/ml) | G'type | Polymerase # | HBsAG# |
|---|---|---|---|---|
| 1.98E+06 | 467 | B | L115M M204I V214A M250I | W196S |
| 1.42E+05 |  |  | PCR-ve |  |
| 1.61E+04 |  |  | PCR-ve |  |
| 2.00E+03 |  |  | PCR-ve |  |
|  |  | B | N53D L115M A181A/V V214A Y221H/Y N236T | C76Y L173L/F |

BIBLIOGRAPHY

Allen et al, *Hepatology* 27(6):1670-1677, 1998
Angus et al, *Gastroenterology.* 125(2):292-297, 2003
Aye et al, *J. Hepatol.* 26:1148-1153, 1997
Bartholomeusz et al, *Intervirology* 40(5-6):337-342 1997
Benhamou et al, *Lancet* 358: 718-723, 2001
Benzaria et al, *J Med Chem.* 39: 4958-4965, 1996
Boyd et al, *Antiviral Chem Chemother.* 32: 358-363, 1987
Calio et al, *Antiviral Res.* 23:77-89, 1994
Das et al, *J. Virol.* 7500:4771-4779, 2001
Dienstag et al, *New England J Med* 333:1657-1661, 1995
Frick et al, *Antimicrob. Agents Chemother.* 37:2285-2292, 1993
Gaillard et al, *Antimicrob Agents Chemother.* 46(4):1005-1013, 2002
Gilson et al, *J Viral Hepat* 6:387-395, 1999
Heathcote et al, *Hepatology* 28:A620, 1998
Hendricks et al, *Am J Clin Pathol* 104:537-46, 1995
Kruger et al, *Hepatology* 22:219A, 1994
Main et al, *J. Viral Hepatitis* 3:211-215, 1996
Norder et al, *J. Gen. Virol.* 74:341-1348, 1993
Perrillo et al, *Hepatology* 32:129-134, 2000
Peters et al, *Transplantation* 68:1912-1914, 1999
Price et al, *Proc. Natl. Acad. Sci. USA* 86(21):8541-8544, 1989
Ren and Nassal, *J. Virol.* 75(3):1104-1116, 2001
Severini et al, *Antimicrobial Agents Chemother.* 39:430-435, 1995
Srinivas and Fridland, *Antimicrob Agents Chemother.* 42(6): 1484-1487, 1998
Stuyver et al, *Hepatology* 33:751-757, 2001
Summers and Mason, *Cell* 29:403-415, 1982
Suo et al, *J Biol Chem.* 273(42):27250-27258. 1998
Tenney et al, *Antimicrob Agents Chemother.* 48:3498-507, 2004
Vere Hodge, *Antiviral Chem Chemother* 4:67-84, 1993
Xiong et al, *Hepatology.* 28(6):1669-1673, 1998
Ying et al, *J Viral Hepat.* 7(1):79-83, 2000
Ying et al, *J Viral Hepat.* 7(2):161-165, 2000

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 13143266_1.TXT, the date of creation of the ASCII text file is Apr. 19, 2012, and the size of the ASCII text file is 65.3 KB.

---

The invention claimed is:

1. A method for determining the potential for a Hepatitis B Virus (HBV) variant to exhibit reduced sensitivity to anti-viral agents adefovir (ADV), lamivudine (LMV) and entecavir (ETV), said method comprising:
   isolating DNA or corresponding mRNA from said HBV;
   amplifying one or more labeled amplicons from said DNA or mRNA by using one or more biotin- or other ligand-labeled primers,
   wherein said one or more labeled primers hybridize to the DNA or mRNA which code for the isoleucine (I), aspartic acid (D), or valine (V) at a position corresponding to position 236 of SEQ ID NO: 28, valine (V) at a position corresponding to position 204 of SEQ ID NO: 28, methionine (M) at a position corresponding to position 180 of SEQ ID NO: 28, glycine (G) at a position corresponding to position 184 of SEQ ID NO: 28, and isoleucine (I) at a position corresponding to position 202 of SEQ ID NO: 28;
   capturing said labeled amplicons by hybridizing to an oligonucleotide immobilized to a solid support;
   detecting one or more a specific nucleic acid fragments by identifying the biotin- or other ligand-labeled amplicon; and
   identifying the presence of a combination of amino acids in a reverse transcriptase (rt) portion of an HBV DNA polymerase comprising an isoleucine (I), aspartic acid (D), or valine (V) at a position corresponding to position 236 of SEQ ID NO: 28, a valine (V) at a position corresponding to position 204 of SEQ ID NO: 28, a methionine (M) at a position corresponding to position 180 of SEQ ID NO: 28, a glycine (G) at a position corresponding to position 184 of SEQ ID NO: 28, and an isoleucine (I) at a position corresponding to position 202 of SEQ ID NO: 28;
   wherein the presence of the combination of amino acids is indicative of reduced sensitivity to said anti-viral agents.

2. The method of claim 1, further comprising identifying the presence of a threonine (T) at a position corresponding to position 85 of SEQ ID NO: 28, wherein said one or more primers hybridize to the DNA or mRNA which codes for a threonine (T) at a position corresponding to position 85 of SEQ ID NO: 28.

3. The method of claim 1, further comprising identifying the presence of a leucine (L) or a valine (V) at a position corresponding to position 42 of SEQ ID NO: 28, a threonine (T) at a position corresponding to position 78 of SEQ ID NO: 28, and an asparagine (N) at a position corresponding to position 128 of SEQ ID NO: 28 wherein said one or more primers hybridize to the DNA or mRNA which codes for a leucine (L) at position 42 of SEQ ID NO: 28, a valine (V) at a position corresponding to position 42 of SEQ ID NO: 28, a threonine (T) at a position corresponding to position 78 of SEQ ID NO: 28, or an asparagine (N) at a position corresponding to position 128 of SEQ ID NO: 28.

4. The method of claim 1, wherein the HBV variant also exhibits reduced sensitivity to tenofovir (TFV).

5. The method of claim 1, wherein in two or more amplicons are amplified.

6. The method of claim 2, wherein in two or more amplicons are amplified.

7. The method of claim 3, wherein in two or more amplicons are amplified.

* * * * *

SEQUENCE LISTING

```
<160> NUMBER OF SEQ ID NOS: 32

<210> SEQ ID NO 1
<211> LENGTH: 23
<212> TYPE: DNA
<213> ORGANISM: Artificial Sequence
<220> FEATURE:
<223> OTHER INFORMATION: PCR primer

<400> SEQUENCE: 1
gcctcatttt gtgggtcacc ata                                           23

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
aaattcgcag tccccaaa                                                 18

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
ttggggtgga gccctcaggc t                                             21

<210> SEQ ID NO 4
<211> LENGTH: 18
<212> TYPE: DNA
<213> ORGANISM: Artificial Sequence
<220> FEATURE:
<223> OTHER INFORMATION: PCR primer

<400> SEQUENCE: 4
gaaaattggt aacagcgg                                                 18
```

```
<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
tctctgacat actttccaat                                                    20

<210> SEQ ID NO 6
<211> LENGTH: 987
<212> TYPE: DNA
<213> ORGANISM: Hepatitis B Virus

<400> SEQUENCE: 6
tccacctcta agagacagtc atcctcaggc catgcagtgg aattccactg ccttccacca        60
agctctgcag gatcccagag tcaggggtct gtattttcct gctggtggct ccagttcagg       120
aacagtaaac cctgctccga atattgcctc tcacatctcg tcaatctccg cgaggactgg       180
ggaccctgtg acgaacatgg agaacatcac atcaggattc ctaggacccc tgctcgtgtt       240
acaggcgggg ttttcttgt tgacaagaat cctcacaata ccgcagagtc tagactcgtg        300
gtggacttct ctcaattttc taggggggatc acccgtgtgt cttggccaaa attcgcagtc       360
cccaacctcc aatcactcac caacctcctg tcctccaatt tgtcctggtt atcgctggat       420
gtgtctgcgg cgttttatca tattcctctt catcctgctg ctatgcctca tcttcttatt       480
ggttcttctg gattatcaag gtatgttgcc cgtttgtcct ctaattccag gatcaacaac       540
aaccagtacg gggccatgca aaacctgcac gactcctgct caaggcaact ctatgtttcc       600
ctcatgttgc tgtacaaaac ctacggatgg aaattgcacc tgtattccca tcccatcgtc       660
ctgggctttc gcaaaatacc tatgggagtg ggcctcagtc cgtttctctt ggctcagttt       720
actagtgcca tttgttcagt ggttcgtagg gctttcccccc actgtttggc tttcagctat       780
atggatgatg tggtattggg ggccaagtct gtacagcatc gtgagtccct ttataccgct       840
gttaccaatt ttcttttgtc tctgggtata catttaaacc ctaacaaaac aaaaagatgg       900
ggttattccc taaacttcat gggttacata attggaagkk ggggaacatt gccacaggat       960
catattgtac aaaagatcaa acactgt                                            987

<210> SEQ ID NO 7
<211> LENGTH: 329
<212> TYPE: PRT
<213> ORGANISM: Hepatitis B Virus
<220> FEATURE:
<221> NAME/KEY: misc_feature
<222> LOCATION: (313)..(313)
<223> OTHER INFORMATION: Xaa can be Arg or Ser
<220> FEATURE:
<221> NAME/KEY: misc_feature
<222> LOCATION: (314)..(314)
<223> OTHER INFORMATION: Xaa can be Gly or Trp

<400> SEQUENCE: 7

Ser Thr Ser Lys Arg Gln Ser Ser Ser Gly His Ala Val Glu Phe His
1               5                   10                  15

Cys Leu Pro Pro Ser Ser Ala Gly Ser Gln Ser Gln Gly Ser Val Phe
            20                  25                  30

Ser Cys Trp Trp Leu Gln Phe Arg Asn Ser Lys Pro Cys Ser Glu Tyr
        35                  40                  45
```

```
Cys Leu Ser His Leu Val Asn Leu Arg Glu Asp Trp Gly Pro Cys Asp
        50                  55                  60
Glu His Gly Glu His His Ile Arg Ile Pro Arg Thr Pro Ala Arg Val
 65                  70                  75                  80
Thr Gly Gly Val Phe Leu Val Asp Lys Asn Pro His Asn Thr Ala Glu
                    85                  90                  95
Ser Arg Leu Val Val Asp Phe Ser Gln Phe Ser Arg Gly Ile Thr Arg
                100                 105                 110
Val Ser Trp Pro Lys Phe Ala Val Pro Asn Leu Gln Ser Leu Thr Asn
                115                 120                 125
Leu Leu Ser Ser Asn Leu Ser Trp Leu Ser Leu Asp Val Ser Ala Ala
130                 135                 140
Phe Tyr His Ile Pro Leu His Pro Ala Ala Met Pro His Leu Leu Ile
145                 150                 155                 160
Gly Ser Ser Gly Leu Ser Arg Tyr Val Ala Arg Leu Ser Ser Asn Ser
                165                 170                 175
Arg Ile Asn Asn Asn Gln Tyr Gly Ala Met Gln Asn Leu His Asp Ser
                180                 185                 190
Cys Ser Arg Gln Leu Tyr Val Ser Leu Met Leu Leu Tyr Lys Thr Tyr
                195                 200                 205
Gly Trp Lys Leu His Leu Tyr Ser His Pro Ile Val Leu Gly Phe Arg
210                 215                 220
Lys Ile Pro Met Gly Val Gly Leu Ser Pro Phe Leu Leu Ala Gln Phe
225                 230                 235                 240
Thr Ser Ala Ile Cys Ser Val Val Arg Arg Ala Phe Pro His Cys Leu
                245                 250                 255
Ala Phe Ser Tyr Met Asp Asp Val Val Leu Gly Ala Lys Ser Val Gln
                260                 265                 270
His Arg Glu Ser Leu Tyr Thr Ala Val Thr Asn Phe Leu Leu Ser Leu
                275                 280                 285
Gly Ile His Leu Asn Pro Asn Lys Thr Lys Arg Trp Gly Tyr Ser Leu
290                 295                 300
Asn Phe Met Gly Tyr Ile Ile Gly Xaa Xaa Gly Thr Leu Pro Gln Asp
305                 310                 315                 320
His Ile Val Gln Lys Ile Lys His Cys
                325

<210> SEQ ID NO 8
<211> LENGTH: 291
<212> TYPE: PRT
<213> ORGANISM: Hepatitis B Virus

<400> SEQUENCE: 8

Pro Pro Leu Arg Asp Ser His Pro Gln Ala Met Gln Trp Asn Ser Thr
 1               5                  10                  15
Ala Phe His Gln Ala Leu Gln Asp Pro Arg Val Arg Gly Leu Tyr Phe
                20                  25                  30
Pro Ala Gly Gly Ser Ser Gly Thr Val Asn Pro Ala Pro Asn Ile
                35                  40                  45
Ala Ser His Ile Ser Ser Ile Ser Ala Arg Thr Gly Asp Pro Val Thr
        50                  55                  60
Asn Met Glu Asn Ile Thr Ser Gly Phe Leu Gly Pro Leu Leu Val Leu
 65                  70                  75                  80
Gln Ala Gly Phe Phe Leu Leu Thr Arg Ile Leu Thr Ile Pro Gln Ser
```

```
                             85                  90                  95
Leu Asp Ser Trp Trp Thr Ser Leu Asn Phe Leu Gly Gly Ser Pro Val
                100                 105                 110

Cys Leu Gly Gln Asn Ser Gln Ser Pro Thr Ser Asn His Ser Pro Thr
                115                 120                 125

Ser Cys Pro Pro Ile Cys Pro Gly Tyr Arg Trp Met Cys Leu Arg Arg
130                 135                 140

Phe Ile Ile Phe Leu Phe Ile Leu Leu Cys Leu Ile Phe Leu Leu
145                 150                 155                 160

Val Leu Leu Asp Tyr Gln Gly Met Leu Pro Val Cys Pro Leu Ile Pro
                165                 170                 175

Gly Ser Thr Thr Thr Ser Thr Gly Pro Cys Lys Thr Cys Thr Thr Pro
                180                 185                 190

Ala Gln Gly Asn Ser Met Phe Pro Ser Cys Cys Cys Thr Lys Pro Thr
                195                 200                 205

Asp Gly Asn Cys Thr Cys Ile Pro Ile Pro Ser Ser Trp Ala Phe Ala
                210                 215                 220

Lys Tyr Leu Trp Glu Trp Ala Ser Val Arg Phe Ser Trp Leu Ser Leu
225                 230                 235                 240

Leu Val Pro Phe Val Gln Trp Phe Val Gly Leu Ser Pro Thr Val Trp
                245                 250                 255

Leu Ser Ala Ile Trp Met Met Trp Tyr Trp Gly Pro Ser Leu Tyr Ser
                260                 265                 270

Ile Val Ser Pro Phe Ile Pro Leu Leu Pro Ile Phe Phe Cys Leu Trp
                275                 280                 285

Val Tyr Ile
290

<210> SEQ ID NO 9
<211> LENGTH: 3197
<212> TYPE: DNA
<213> ORGANISM: Hepatitis B Virus

<400> SEQUENCE: 9
atgcccctat cttatcaaca cttccggaaa ctactgttgt tagacgacga ggcaggtccc        60
ctagaagaag aactccctcg cctcgcagac gaaggtctca atcgccgcgt cgcagaagat       120
ctaaatctcg gaatctcaa tgttagtatc ccttggactc ataaggtggg aaactttact       180
gggctttatt cttctactgt acctgtcttt aatcctgact ggcaaactcc ctcttttcct       240
cacattcatt tgaaagagga tattattgat agatgtcaac aatatgtagg ccctcttaca       300
gttaacgaaa aaggagatt aaaattgatt atgcctgcta gattctatcc taaccgtacc       360
aaatatttgc cctagataa aggcattaar cctattatc ctgaacacac agttaatcat       420
tacttccaaa ctaggcatta yttacatact ctgtggaagg ctggtatttt atataagaga       480
gaaactactc gcagcgcctc attctgtggg tcaccatatt cttgggaaca agagctacag       540
catgggaggt tcgtattcca aacctcgaca aggcatgggg acgaatcttt ctgttcccaa       600
tcctctggga ttctttcccg atcaccagtt ggacccggca ttcagagcca attcaaacaa       660
tccagattgg gacttcaacc ccaacaagga tcaatggcck gcggcacacc aggtaggagt       720
gggatccttc gggccagggt tcactccacc acacggcaat cttttgggggt ggagccctca       780 ggctcagggc atrttgacaa cagtrccagc rgcgcctcct cctgcctcca ccaatcggca       840
gtcaggaaga cagcctactc ccatctctcc acctctraga gacagtcatc ctcaggccac       900
```

```
attccaccaa gctctgctag atcccagagt gaggggccta tacyttcctg ctggtggctc    960
cagttccgga acagtraacc ctgttccgac tactgcctct cccatatcgt caatcttctc   1020
gaggactggg gaccctgcac cgaagatgga gagcaccaca tcaggattcc taggacccct   1080
gctcgtgtta caggcggggt ttttcttgtt gacaagaatc ctcacaatac cacagagtct   1140
agactcgtgg tggacttctc tcaatttttct aggggggagca cccacgtgtc ctggccaaaa   1200
tttgcagtcc ccaacctcca atcactcacc aacctcttgt cctccaattt gtcctggtta   1260
tcgctggatg tgtctgcggc gttttatcat attcctcttc atcctgctgc tatgcctcay   1320
cttcttgttg gttcttctgg actaycaagg tatgttgccc gtttgtcctc tacttccagg   1380
aacatcaacy ccagcacgg gaccatgcaa gacctgcacg actcctgctc aaggaacctc   1440
tatgttttccc tcttgttgct gtacaaaacc ttcggacgga aattgcactt gtattcccat   1500
cccatcatct tgggctttcg caagattcct atgggagtgg gcctcagtcc gtttctcatg   1560
gctcagtttt ctagtgccat tgttcagtg gttcgtaggg ctttccccca ctgtttggct   1620
ttcagttatg tggatgatgt ggtattgggg gccaagtctg tacaacatct tgaatcccctt   1680
tttaccgctg ttaccaattt tcttttgtct ttgggtatac atttaaaccc tactaaaact   1740
aaacgttggg gctactccct tcacttcatg ggwtatgtaa ttggaagttg gggtaccttaa   1800
ccacaggaac atattgtaca caaaatcaaa caatgttttc ggaaacttcc tataaataga   1860
cctattgatt ggaaagtatg tcaacgaatt gtggggcttc taggctttgc cgctcccttt   1920
acacaatgtg gttacccagc attaatgcct ttgtatgcat gtatacaagc taaacaggct   1980
ttcacttttt cgccaactta caaggccttt ctgtgtaaac aatatctgca cctttacccc   2040
gttgctcggc aacggtcagg tctttgccaa gtgtttgctg acgcaacccc cactggttgg   2100
ggcttggcca taggccatca gcgcmtgcgt ggaaccttg tggctcctct gccgatccat   2160
actgcggaac tcctagcagc ttgtttttgct cgcagccggt ctggagcaaa cattatcggc   2220
accgacaact ctgttgtcct ctctcggaaa tacacctcct ttccatggct gctaggctgt   2280
gctgccaact ggatcctgcg cgggacgtcc tttgtctacg tcccgtcrgc gctgaatccc   2340
gcggacgacc cgtctcgggg caggttggga ctctaccgtc cccttcttcg tctgccgttc   2400
cggccgacca cggggcgcac ctctctttac gcggtctccc cgtctgtgcc ttctcatctg   2460
ccggaccgtg tgcacttcgc ttcacctctg cacgtgcat ggaaaccacc gtgaacgccy   2520
gccaggtctt gcccaaggtc ttacataaga ggactcttgg actctcagca atgtcaacga   2580
ccgaccttga ggcatacttc aaagactgtg tatttacaga ctgggaggag ttgggggagg   2640
agactaggtt aatgatcttt gtactaggag gctgtaggca taaattggtc tgttcaccag   2700
caccatgcaa ctttttcacc tctgcctaat catctcttgt tcatgtccca ctgttcaagc   2760
ctccaagctg tgccttgggt ggctttgggg catggacatt gacacctata aagaatttgg   2820
agcttctgtg gagttactct cttttttgcc ttctgacttc tttccgaata ttcgtgatct   2880
cctcgacacc gcctctgctc tgcatcggga kgccttagag tctcmggaac attgttcmcc   2940
tcaccataca gcactaaggc aagctattgt gtgttggggt gagttgatga atctggccac   3000
ctgggtggga agtaatttgg aagacccagc atccagggaa ttagtagtaa gctatgtcaa   3060
cgttaatatg ggcctaaaaa tcagacaact attgtggttt cacatttcct gtcttacttt   3120
tggaagagaa actgttcttg agtatttggt gtcttttgga gtgtggattc gcactcctcc   3180
cgcttacaga ccaccaa                                                  3197
```

```
<210> SEQ ID NO 10
<211> LENGTH: 837
<212> TYPE: PRT
<213> ORGANISM: Hepatitis B Virus
<220> FEATURE:
<221> NAME/KEY: misc_feature
<222> LOCATION: (234)..(234)
<223> OTHER INFORMATION: Xaa can be Gly or Cys
<220> FEATURE:
<221> NAME/KEY: misc_feature
<222> LOCATION: (265)..(265)
<223> OTHER INFORMATION: Xaa can be Ile or Val
<220> FEATURE:
<221> NAME/KEY: misc_feature
<222> LOCATION: (269)..(269)
<223> OTHER INFORMATION: Xaa can be Thr or Ala
<220> FEATURE:
<221> NAME/KEY: misc_feature
<222> LOCATION: (271)..(271)
<223> OTHER INFORMATION: Xaa can be Ser or Gly
<220> FEATURE:
<221> NAME/KEY: misc_feature
<222> LOCATION: (293)..(293)
<223> OTHER INFORMATION: Xaa can be Lys or Glu
<220> FEATURE:
<221> NAME/KEY: misc_feature
<222> LOCATION: (315)..(315)
<223> OTHER INFORMATION: Xaa can be Pro or Leu
<220> FEATURE:
<221> NAME/KEY: misc_feature
<222> LOCATION: (326)..(326)
<223> OTHER INFORMATION: Xaa can be Lys or Glu
<220> FEATURE:
<221> NAME/KEY: misc_feature
<222> LOCATION: (449)..(449)
<223> OTHER INFORMATION: Xaa can be Pro or Ser
<220> FEATURE:
<221> NAME/KEY: misc_feature
<222> LOCATION: (464)..(464)
<223> OTHER INFORMATION: Xaa can be His or Tyr
<220> FEATURE:
<221> NAME/KEY: misc_feature
<222> LOCATION: (709)..(709)
<223> OTHER INFORMATION: Xaa can be Met or Leu

<400> SEQUENCE: 10

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Asp Trp Gln Thr Pro Ser Phe Pro
65                  70                  75                  80

His Ile His Leu Lys Glu Asp Ile Ile Asp Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Arg Thr Lys Tyr Leu Pro Leu Asp Lys Gly
        115                 120                 125

Ile Lys Pro Tyr Tyr Pro Glu His Thr Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175
```

```
Gln Glu Leu Gln His Gly Arg Phe Val Phe Gln Thr Ser Thr Arg His
            180                 185                 190

Gly Asp Glu Ser Phe Cys Ser Gln Ser Ser Gly Ile Leu Ser Arg Ser
        195                 200                 205

Pro Val Gly Pro Gly Ile Gln Ser Gln Phe Lys Gln Ser Arg Leu Gly
    210                 215                 220

Leu Gln Pro Gln Gln Gly Ser Met Ala Xaa Gly Thr Pro Gly Arg Ser
225                 230                 235                 240

Gly Ile Leu Arg Ala Arg Val His Ser Thr Thr Arg Gln Ser Phe Gly
                245                 250                 255

Val Glu Pro Ser Gly Ser Gly His Xaa Asp Asn Ser Xaa Ser Xaa Ala
            260                 265                 270

Ser Ser Cys Leu His Gln Ser Ala Val Arg Lys Thr Ala Tyr Ser His
        275                 280                 285

Leu Ser Thr Ser Xaa Arg Gln Ser Ser Ser Gly His Ile Pro Pro Ser
    290                 295                 300

Ser Ala Arg Ser Gln Ser Glu Gly Pro Ile Xaa Ser Cys Trp Trp Leu
305                 310                 315                 320

Gln Phe Arg Asn Ser Xaa Pro Cys Ser Asp Tyr Cys Leu Ser His Ile
                325                 330                 335

Val Asn Leu Leu Glu Asp Trp Gly Pro Cys Thr Glu Asp Gly Glu His
            340                 345                 350

His Ile Arg Ile Pro Arg Thr Pro Ala Arg Val Thr Gly Gly Val Phe
        355                 360                 365

Leu Val Asp Lys Asn Pro His Asn Thr Thr Glu Ser Arg Leu Val Val
    370                 375                 380

Asp Phe Ser Gln Phe Ser Arg Gly Ser Thr His Val Ser Trp Pro Lys
385                 390                 395                 400

Phe Ala Val Pro Asn Leu Gln Ser Leu Thr Asn Leu Leu Ser Ser Asn
                405                 410                 415

Leu Ser Trp Leu Ser Leu Asp Val Ser Ala Ala Phe Tyr His Ile Pro
            420                 425                 430

Leu His Pro Ala Ala Met Pro His Leu Leu Val Gly Ser Ser Gly Leu
        435                 440                 445

Xaa Arg Tyr Val Ala Arg Leu Ser Ser Thr Ser Arg Asn Ile Asn Xaa
    450                 455                 460

Gln His Gly Thr Met Gln Asp Leu His Asp Ser Cys Ser Arg Asn Leu
465                 470                 475                 480

Tyr Val Ser Leu Leu Leu Leu Tyr Lys Thr Phe Gly Arg Lys Leu His
                485                 490                 495

Leu Tyr Ser His Pro Ile Ile Leu Gly Phe Arg Lys Ile Pro Met Gly
            500                 505                 510

Val Gly Leu Ser Pro Phe Leu Met Ala Gln Phe Ser Ser Ala Ile Cys
        515                 520                 525

Ser Val Val Arg Arg Ala Phe Pro His Cys Leu Ala Phe Ser Tyr Val
    530                 535                 540

Asp Asp Val Val Leu Gly Ala Lys Ser Val Gln His Leu Glu Ser Leu
545                 550                 555                 560

Phe Thr Ala Val Thr Asn Phe Leu Leu Ser Leu Gly Ile His Leu Asn
                565                 570                 575

Pro Thr Lys Thr Lys Arg Trp Gly Tyr Ser Leu His Phe Met Gly Tyr
            580                 585                 590
```

```
Val Ile Gly Ser Trp Gly Thr Leu Pro Gln Glu His Ile His Lys
            595                 600                 605

Ile Lys Gln Cys Phe Arg Lys Leu Pro Ile Asn Arg Pro Ile Asp Trp
610                 615                 620

Lys Val Cys Gln Arg Ile Val Gly Leu Leu Gly Phe Ala Ala Pro Phe
625                 630                 635                 640

Thr Gln Cys Gly Tyr Pro Ala Leu Met Pro Leu Tyr Ala Cys Ile Gln
                645                 650                 655

Ala Lys Gln Ala Phe Thr Phe Ser Pro Thr Tyr Lys Ala Phe Leu Cys
            660                 665                 670

Lys Gln Tyr Leu His Leu Tyr Pro Val Ala Arg Gln Arg Ser Gly Leu
        675                 680                 685

Cys Gln Val Phe Ala Asp Ala Thr Pro Thr Gly Trp Gly Leu Ala Ile
    690                 695                 700

Gly His Gln Arg Xaa Arg Gly Thr Phe Val Ala Pro Leu Pro Ile His
705                 710                 715                 720

Thr Ala Glu Leu Leu Ala Ala Cys Phe Ala Arg Ser Arg Ser Gly Ala
                725                 730                 735

Asn Ile Ile Gly Thr Asp Asn Ser Val Val Leu Ser Arg Lys Tyr Thr
            740                 745                 750

Ser Phe Pro Trp Leu Leu Gly Cys Ala Ala Asn Trp Ile Leu Arg Gly
        755                 760                 765

Thr Ser Phe Val Tyr Val Pro Ser Ala Leu Asn Pro Ala Asp Asp Pro
    770                 775                 780

Ser Arg Gly Arg Leu Gly Leu Tyr Arg Pro Leu Leu Arg Leu Pro Phe
785                 790                 795                 800

Arg Pro Thr Thr Gly Arg Thr Ser Leu Tyr Ala Val Ser Pro Ser Val
                805                 810                 815

Pro Ser His Leu Pro Asp Arg Val His Phe Ala Ser Pro Leu His Val
            820                 825                 830

Ala Trp Lys Pro Pro
        835

<210> SEQ ID NO 11
<211> LENGTH: 226
<212> TYPE: PRT
<213> ORGANISM: Hepatitis B Virus
<220> FEATURE:
<221> NAME/KEY: misc_feature
<222> LOCATION: (92)..(92)
<223> OTHER INFORMATION: Xaa can be Thr or Ile

<400> SEQUENCE: 11

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Leu Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Xaa Phe Leu Leu Val
            85                  90                  95

Leu Leu Asp Tyr Gln Gly Met Leu Pro Val Cys Pro Leu Leu Pro Gly
```

```
            100                 105                 110
Thr Ser Thr Thr Ser Thr Gly Pro Cys Lys Thr Cys Thr Thr Pro Ala
            115                 120                 125

Gln Gly Thr Ser Met Phe Pro Ser Cys Cys Cys Thr Lys Pro Ser Asp
            130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Phe Leu
                165                 170                 175

Val Pro Phe Val Gln Trp Phe Val Gly Leu Ser Pro Thr Val Trp Leu
            180                 185                 190

Ser Val Met Trp Met Met Trp Tyr Trp Gly Pro Ser Leu Tyr Asn Ile
            195                 200                 205

Leu Asn Pro Phe Leu Pro Leu Leu Pro Ile Phe Phe Cys Leu Trp Val
    210                 215                 220

Tyr Ile
225

<210> SEQ ID NO 12
<211> LENGTH: 984
<212> TYPE: DNA
<213> ORGANISM: Hepatitis B Virus

<400> SEQUENCE: 12
tccgcctcct gcctctacca atcgacagtc aggacggcag cctaccccgc tgtctccacc      60
tctgagaatc actcatcctc aggccatgca gtggaactcc acaaccttcc accaaactct     120
gcaagatccc aragtgagag gcctgkmtct ccctgctggt ggctccagtt caggaacagt     180
aaaccctgtt ccgactactg cctctcccat atcgwcaatc ttctcgagga ttggggaccc     240
tgcgctgaac atggagaaca tcacatcagg attcctagga cccctgctcg tgttacaggc     300 ggggttttc ttgttgacaa gaatcctcac aataccgcag agtctagact cgtggtggac      360
ttctctcaat tttctagggg gaactaccgt gtgtcttggc caaaattcgc agtccccaac     420
ctccaatcac tcaccaacct cctgtcctcc aacttgtcct ggttatcgct ggatgtgtct     480
gcggcgtttt atcatcttcc tcttcatcct gctgctatgc ctcatcttct gttggttct      540 tctggactat caaggtatgt tgcccgtttg tcctctaatt ccaggatcat caaccaccag     600
cacgggaccc tgcagaacct gcacgactcc tgctcaagga acctctatgt atccctcctg     660
ttgctgtaca aaaccttcgg atggaaactg cacctgtatt cccatcccat catcctgggc     720
tttcggaaaa ttcctatggg agtgggcctc agcccgtttc tcttggctca gtttactagt     780
gccatttgtt cagtggttcg tagggctttc ccccattgtt tggctttcag ttatatggat     840
gatgtggtat tgggggccaa gtctgtatcg catcttgagt ccctttttac cgctgttacc     900
aattttcttt tgtctttggg tatacattta aaccctaaca aacaaaaar awggggttat     960 tctctaaatt tcatgggcta tgtc                                             984

<210> SEQ ID NO 13
<211> LENGTH: 328
<212> TYPE: PRT
<213> ORGANISM: Hepatitis B Virus
<220> FEATURE:
<221> NAME/KEY: misc_feature
<222> LOCATION: (49)..(49)
<223> OTHER INFORMATION: Xaa can be Gly or Val
<220> FEATURE:
<221> NAME/KEY: misc_feature
```

<222> LOCATION: (72)..(72)
<223> OTHER INFORMATION: Xaa can be Asp or Val
<220> FEATURE:
<221> NAME/KEY: misc_feature
<222> LOCATION: (317)..(317)
<223> OTHER INFORMATION: Xaa can be Lys or Arg
<220> FEATURE:
<221> NAME/KEY: misc_feature
<222> LOCATION: (318)..(318)
<223> OTHER INFORMATION: Xaa can be Arg or Trp

<400> SEQUENCE: 13

```
Ser Ala Ser Cys Leu Tyr Gln Ser Thr Val Arg Thr Ala Ala Tyr Pro
1               5                   10                  15

Ala Val Ser Thr Ser Glu Asn His Ser Ser Gly His Ala Val Glu
            20                  25                  30

Leu His Asn Leu Pro Pro Asn Ser Ala Arg Ser Gln Ser Glu Arg Pro
            35                  40                  45

Xaa Ser Pro Cys Trp Trp Leu Gln Phe Arg Asn Ser Lys Pro Cys Ser
        50                  55                  60

Asp Tyr Cys Leu Ser His Ile Xaa Asn Leu Leu Glu Asp Trp Gly Pro
65                  70                  75                  80

Cys Ala Glu His Gly Glu His Ile Arg Ile Pro Arg Thr Pro Ala
                85                  90                  95

Arg Val Thr Gly Gly Val Phe Leu Val Asp Lys Asn Pro His Asn Thr
            100                 105                 110

Ala Glu Ser Arg Leu Val Val Asp Phe Ser Gln Phe Ser Arg Gly Asn
        115                 120                 125

Tyr Arg Val Ser Trp Pro Lys Phe Ala Val Pro Asn Leu Gln Ser Leu
    130                 135                 140

Thr Asn Leu Leu Ser Ser Asn Leu Ser Trp Leu Ser Leu Asp Val Ser
145                 150                 155                 160

Ala Ala Phe Tyr His Leu Pro Leu His Pro Ala Ala Met Pro His Leu
                165                 170                 175

Leu Val Gly Ser Ser Gly Leu Ser Arg Tyr Val Ala Arg Leu Ser Ser
            180                 185                 190

Asn Ser Arg Ile Ile Asn His Gln His Gly Thr Leu Gln Asn Leu His
        195                 200                 205

Asp Ser Cys Ser Arg Asn Leu Tyr Val Ser Leu Leu Leu Leu Tyr Lys
    210                 215                 220

Thr Phe Gly Trp Lys Leu His Leu Tyr Ser His Pro Ile Ile Leu Gly
225                 230                 235                 240

Phe Arg Lys Ile Pro Met Gly Val Gly Leu Ser Pro Phe Leu Leu Ala
                245                 250                 255

Gln Phe Thr Ser Ala Ile Cys Ser Val Val Arg Arg Ala Phe Pro His
            260                 265                 270

Cys Leu Ala Phe Ser Tyr Met Asp Asp Val Val Leu Gly Ala Lys Ser
        275                 280                 285

Val Ser His Leu Glu Ser Leu Phe Thr Ala Val Thr Asn Phe Leu Leu
    290                 295                 300

Ser Leu Gly Ile His Leu Asn Pro Asn Lys Thr Lys Xaa Xaa Gly Tyr
305                 310                 315                 320

Ser Leu Asn Phe Met Gly Tyr Val
                325
```

<210> SEQ ID NO 14
<211> LENGTH: 308

```
<212> TYPE: PRT
<213> ORGANISM: Hepatitis B Virus
<220> FEATURE:
<221> NAME/KEY: misc_feature
<222> LOCATION: (43)..(43)
<223> OTHER INFORMATION: Xaa can be Lys or Arg
<220> FEATURE:
<221> NAME/KEY: misc_feature
<222> LOCATION: (48)..(48)
<223> OTHER INFORMATION: Xaa can be Asp, Ala, Tyr or Ser
<220> FEATURE:
<221> NAME/KEY: misc_feature
<222> LOCATION: (71)..(71)
<223> OTHER INFORMATION: Xaa can be Thr or Ser

<400> SEQUENCE: 14

Pro Pro Ala Ser Thr Asn Arg Gln Ser Gly Arg Gln Pro Thr Pro Leu
1               5                   10                  15

Ser Pro Pro Leu Arg Ile Thr His Pro Gln Ala Met Gln Trp Asn Ser
            20                  25                  30

Thr Thr Phe His Gln Thr Leu Gln Asp Pro Xaa Val Arg Gly Leu Xaa
        35                  40                  45

Leu Pro Ala Gly Gly Ser Ser Gly Thr Val Asn Pro Val Pro Thr
50                  55                  60

Thr Ala Ser Pro Ile Ser Xaa Ile Phe Ser Arg Ile Gly Asp Pro Ala
65                  70                  75                  80

Leu Asn Met Glu Asn Ile Thr Ser Gly Phe Leu Gly Pro Leu Leu Val
                85                  90                  95

Leu Gln Ala Gly Phe Phe Leu Leu Thr Arg Ile Leu Thr Ile Pro Gln
            100                 105                 110

Ser Leu Asp Ser Trp Trp Thr Ser Leu Asn Phe Leu Gly Gly Thr Thr
        115                 120                 125

Val Cys Leu Gly Gln Asn Ser Gln Ser Pro Thr Ser Asn His Ser Pro
130                 135                 140

Thr Ser Cys Pro Pro Thr Cys Pro Gly Tyr Arg Trp Met Cys Leu Arg
145                 150                 155                 160

Arg Phe Ile Ile Phe Leu Phe Ile Leu Leu Leu Cys Leu Ile Phe Leu
                165                 170                 175

Leu Val Leu Leu Asp Tyr Gln Gly Met Leu Pro Val Cys Pro Leu Ile
            180                 185                 190

Pro Gly Ser Ser Thr Thr Ser Thr Gly Pro Cys Arg Thr Cys Thr Thr
        195                 200                 205

Pro Ala Gln Gly Thr Ser Met Tyr Pro Ser Cys Cys Cys Thr Lys Pro
210                 215                 220

Ser Asp Gly Asn Cys Thr Cys Ile Pro Ile Pro Ser Ser Trp Ala Phe
225                 230                 235                 240

Gly Lys Phe Leu Trp Glu Trp Ala Ser Ala Arg Phe Ser Trp Leu Ser
                245                 250                 255

Leu Leu Val Pro Phe Val Gln Trp Phe Val Gly Leu Ser Pro Ile Val
            260                 265                 270

Trp Leu Ser Val Ile Trp Met Met Trp Tyr Trp Gly Pro Ser Leu Tyr
        275                 280                 285

Arg Ile Leu Ser Pro Phe Leu Pro Leu Leu Pro Ile Phe Phe Cys Leu
290                 295                 300

Trp Val Tyr Ile
305

<210> SEQ ID NO 15
```

<211> LENGTH: 580
<212> TYPE: DNA
<213> ORGANISM: Hepatitis B Virus

<400> SEQUENCE: 15

```
ttgtcctggt tatcgctgga tgtgtctgcg gcgttttatc atcttcctct tcatcctgct     60
gctatgcctc atcttcttgt tggttcttct ggactatcaa ggtatgttgc ccgtctgtcc    120
tctagttccg agatcttcaa ccaccagcgc gggacaatgc agaacctgca cgactactgc    180
tcaaggaacc tctatgtatc cctcctgttg ctgtaccaaa ccttcggacg gaaattgcac    240
ctgtattccc atcccatcat cctgggcttt cggaaaattc ctatgggagt gggcctcagt    300
ccgtttctcc tggctcagtt tgctagtgcc atttgttcag tggttcgtag ggctttcccc    360
cactgtttgg ctttcagtta tatggatgat gtggtattgg gggccaagtc tgtacaacat    420
cttgagtccc tttttaccgc tgttaccaat tttcttttgt ctttgggtat acatttaaat    480
cctaacaaaa ctaaaagatg gggttactct ttaaatttca tgggctatgt cattggatgt    540
catgggtcct tgccacaaga tcacatcata cagaaaatca                          580
```

<210> SEQ ID NO 16
<211> LENGTH: 193
<212> TYPE: PRT
<213> ORGANISM: Hepatitis B Virus

<400> SEQUENCE: 16

```
Leu Ser Trp Leu Ser Leu Asp Val Ser Ala Ala Phe Tyr His Leu Pro
1               5                   10                  15

Leu His Pro Ala Ala Met Pro His Leu Leu Val Gly Ser Ser Gly Leu
                20                  25                  30

Ser Arg Tyr Val Ala Arg Leu Ser Ser Ser Ser Glu Ile Phe Asn His
            35                  40                  45

Gln Arg Gly Thr Met Gln Asn Leu His Asp Tyr Cys Ser Arg Asn Leu
        50                  55                  60

Tyr Val Ser Leu Leu Leu Leu Tyr Gln Thr Phe Gly Arg Lys Leu His
65                  70                  75                  80

Leu Tyr Ser His Pro Ile Ile Leu Gly Phe Arg Lys Ile Pro Met Gly
                85                  90                  95

Val Gly Leu Ser Pro Phe Leu Leu Ala Gln Phe Ala Ser Ala Ile Cys
            100                 105                 110

Ser Val Val Arg Arg Ala Phe Pro His Cys Leu Ala Phe Ser Tyr Met
        115                 120                 125

Asp Asp Val Val Leu Gly Ala Lys Ser Val Gln His Leu Glu Ser Leu
    130                 135                 140

Phe Thr Ala Val Thr Asn Phe Leu Leu Ser Leu Gly Ile His Leu Asn
145                 150                 155                 160

Pro Asn Lys Thr Lys Arg Trp Gly Tyr Ser Leu Asn Phe Met Gly Tyr
                165                 170                 175

Val Ile Gly Cys His Gly Ser Leu Pro Gln Asp His Ile Ile Gln Lys
            180                 185                 190

Ile
```

<210> SEQ ID NO 17
<211> LENGTH: 158
<212> TYPE: PRT
<213> ORGANISM: Hepatitis B Virus

<400> SEQUENCE: 17

Cys Pro Gly Tyr Arg Trp Met Cys Leu Arg Arg Phe Ile Ile Phe Leu
1               5                   10                  15

Phe Ile Leu Leu Leu Cys Leu Ile Phe Leu Leu Val Leu Leu Asp Tyr
            20                  25                  30

Gln Gly Met Leu Pro Val Cys Pro Leu Val Pro Arg Ser Ser Thr Thr
            35                  40                  45

Ser Ala Gly Gln Cys Arg Thr Cys Thr Thr Thr Ala Gln Gly Thr Ser
50                  55                  60

Met Tyr Pro Ser Cys Cys Cys Thr Lys Pro Ser Asp Gly Asn Cys Thr
65                  70                  75                  80

Cys Ile Pro Ile Pro Ser Ser Trp Ala Phe Gly Lys Phe Leu Trp Glu
                85                  90                  95

Trp Ala Ser Val Arg Phe Ser Trp Leu Ser Leu Leu Val Pro Phe Val
                100                 105                 110

Gln Trp Phe Val Gly Leu Ser Pro Thr Val Trp Leu Ser Val Ile Trp
        115                 120                 125

Met Met Trp Tyr Trp Gly Pro Ser Leu Tyr Asn Ile Leu Ser Pro Phe
130                 135                 140

Leu Pro Leu Leu Pro Ile Phe Phe Cys Leu Trp Val Tyr Ile
145                 150                 155

<210> SEQ ID NO 18
<211> LENGTH: 965
<212> TYPE: DNA
<213> ORGANISM: Hepatitis B Virus

<400> SEQUENCE: 18
ctaccaatcg acagtcaggg aggcagccta ccccgctgtc tccacctttg agaaacactc      60
atcctcaggc catgcagtgg aactccacaa cttttccacca aactctacaa gatcccaggg    120
tgagaggcct gtatttccct gctggtggct ccagttcagg aacagtaaac cctgttccga    180
ctactgcctc tcccatatcg tcaatcttct cgaggattgg ggaccctgcg ctgaacatgg    240
agaacatcac atcaggattc ctaggacccc tgctcgtgtt acaggcgggg ttttcttgt     300 tgacaaaaat cctcacaata ccgcagagtc tagactcgtg gtggacttct ctcaattttc    360 taggggaac caccgtgtgt cttggccaaa attcgcagtc cccaacctcc aatcactcac     420
caacctcctg tcctccgact tgtcctggtt atcgctggat gtgtctgcgg cgttctatca    480
tattcctctt catcctgctg ctatgcctca tcttcttgtt ggttcttctg gactatcaag    540
gtatgttgcc cgtctgtcct ctaattccag gatcktcaac caccagcgcg ggaccatgca    600
gaacctgcac gactactgct caaggaacct ctatgtatcc ctcctgttgt tgtaccaaac    660
cttcggacgg aaattgcacc tgtattccca tcccatcatc ctgggctttc ggaaaattcc    720
tatgggagtg ggcctcagcc cgtttctcct ggctcagttt actagtgcca tttgttcagt    780
ggttcgtagg gctttccccc actgtttggc tttcagttat atggatgatg tggtattggg    840
ggccaagtct gttcagcmtc gtgaagccct ttttaccgct gttaccaatt tcttwtgtc     900 tttgggtaya catttaaacc ctaacaaaam tagaagatgg ggttattcct taaatttcat    960
gggct                                                                965

<210> SEQ ID NO 19
<211> LENGTH: 321
<212> TYPE: PRT
<213> ORGANISM: Hepatitis B Virus
<220> FEATURE:

```
<221> NAME/KEY: misc_feature
<222> LOCATION: (192)..(192)
<223> OTHER INFORMATION: Xaa can be Val or Phe
<220> FEATURE:
<221> NAME/KEY: misc_feature
<222> LOCATION: (286)..(286)
<223> OTHER INFORMATION: Xaa can be His or Pro
<220> FEATURE:
<221> NAME/KEY: misc_feature
<222> LOCATION: (299)..(299)
<223> OTHER INFORMATION: Xaa can be Met or Leu
<220> FEATURE:
<221> NAME/KEY: misc_feature
<222> LOCATION: (303)..(303)
<223> OTHER INFORMATION: Xaa can be Thr or Ile
<220> FEATURE:
<221> NAME/KEY: misc_feature
<222> LOCATION: (310)..(310)
<223> OTHER INFORMATION: Xaa can be Asn or Thr

<400> SEQUENCE: 19
```

| | | | | | | | | | | | | | | | |
|---|---|---|---|---|---|---|---|---|---|---|---|---|---|---|---|
| Tyr | Gln | Ser | Thr | Val | Arg | Glu | Ala | Ala | Tyr | Pro | Ala | Val | Ser | Thr | Phe |
| 1 | | | | 5 | | | | | 10 | | | | | 15 | |
| Glu | Lys | His | Ser | Ser | Gly | His | Ala | Val | Glu | Leu | His | Asn | Phe | Pro | |
| | | | 20 | | | | | 25 | | | | | 30 | | |
| Pro | Asn | Ser | Thr | Arg | Ser | Gln | Gly | Glu | Arg | Pro | Val | Phe | Pro | Cys | Trp |
| | | | 35 | | | | | 40 | | | | | 45 | | |
| Trp | Leu | Gln | Phe | Arg | Asn | Ser | Lys | Pro | Cys | Ser | Asp | Tyr | Cys | Leu | Ser |
| | 50 | | | | | 55 | | | | | 60 | | | | |
| His | Ile | Val | Asn | Leu | Leu | Glu | Asp | Trp | Gly | Pro | Cys | Ala | Glu | His | Gly |
| 65 | | | | | 70 | | | | | 75 | | | | | 80 |
| Glu | His | His | Ile | Arg | Ile | Pro | Arg | Thr | Pro | Ala | Arg | Val | Thr | Gly | Gly |
| | | | | 85 | | | | | 90 | | | | | 95 | |
| Val | Phe | Leu | Val | Asp | Lys | Asn | Pro | His | Asn | Thr | Ala | Glu | Ser | Arg | Leu |
| | | | 100 | | | | | 105 | | | | | 110 | | |
| Val | Val | Asp | Phe | Ser | Gln | Phe | Ser | Arg | Gly | Asn | His | Arg | Val | Ser | Trp |
| | | | 115 | | | | | 120 | | | | | 125 | | |
| Pro | Lys | Phe | Ala | Val | Pro | Asn | Leu | Gln | Ser | Leu | Thr | Asn | Leu | Leu | Ser |
| | 130 | | | | | 135 | | | | | 140 | | | | |
| Ser | Asp | Leu | Ser | Trp | Leu | Ser | Leu | Asp | Val | Ser | Ala | Ala | Phe | Tyr | His |
| 145 | | | | | 150 | | | | | 155 | | | | | 160 |
| Ile | Pro | Leu | His | Pro | Ala | Ala | Met | Pro | His | Leu | Leu | Val | Gly | Ser | Ser |
| | | | | 165 | | | | | 170 | | | | | 175 | |
| Gly | Leu | Ser | Arg | Tyr | Val | Ala | Arg | Leu | Ser | Ser | Asn | Ser | Arg | Ile | Xaa |
| | | | 180 | | | | | 185 | | | | | 190 | | |
| Asn | His | Gln | Arg | Gly | Thr | Met | Gln | Asn | Leu | His | Asp | Tyr | Cys | Ser | Arg |
| | | | | 195 | | | | | 200 | | | | | 205 | |
| Asn | Leu | Tyr | Val | Ser | Leu | Leu | Leu | Leu | Tyr | Gln | Thr | Phe | Gly | Arg | Lys |
| | 210 | | | | | 215 | | | | | 220 | | | | |
| Leu | His | Leu | Tyr | Ser | His | Pro | Ile | Ile | Leu | Gly | Phe | Arg | Lys | Ile | Pro |
| 225 | | | | | 230 | | | | | 235 | | | | | 240 |
| Met | Gly | Val | Gly | Leu | Ser | Pro | Phe | Leu | Leu | Ala | Gln | Phe | Thr | Ser | Ala |
| | | | | 245 | | | | | 250 | | | | | 255 | |
| Ile | Cys | Ser | Val | Val | Arg | Arg | Ala | Phe | Pro | His | Cys | Leu | Ala | Phe | Ser |
| | | | 260 | | | | | 265 | | | | | 270 | | |
| Tyr | Met | Asp | Asp | Val | Val | Leu | Gly | Ala | Lys | Ser | Val | Gln | Xaa | Arg | Glu |
| | | 275 | | | | | 280 | | | | | 285 | | | |
| Ala | Leu | Phe | Thr | Ala | Val | Thr | Asn | Phe | Leu | Xaa | Ser | Leu | Gly | Xaa | His |
| | 290 | | | | | 295 | | | | | 300 | | | | |

Leu Asn Pro Asn Lys Xaa Arg Arg Trp Gly Tyr Ser Leu Asn Phe Met
305                 310                 315                 320

Gly

<210> SEQ ID NO 20
<211> LENGTH: 304
<212> TYPE: PRT
<213> ORGANISM: Hepatitis B Virus
<220> FEATURE:
<221> NAME/KEY: misc_feature
<222> LOCATION: (286)..(286)
<223> OTHER INFORMATION: Xaa can be Ile or Leu
<220> FEATURE:
<221> NAME/KEY: misc_feature
<222> LOCATION: (298)..(298)
<223> OTHER INFORMATION: Xaa can be Leu or Phe
<220> FEATURE:
<221> NAME/KEY: misc_feature
<222> LOCATION: (303)..(303)
<223> OTHER INFORMATION: Xaa can be His or Tyr

<400> SEQUENCE: 20

Thr Asn Arg Gln Ser Gly Arg Gln Pro Thr Pro Leu Ser Pro Pro Leu
1               5                   10                  15

Arg Asn Thr His Pro Gln Ala Met Gln Trp Asn Ser Thr Thr Phe His
                20                  25                  30

Gln Thr Leu Gln Asp Pro Arg Val Arg Gly Leu Tyr Phe Pro Ala Gly
            35                  40                  45

Gly Ser Ser Ser Gly Thr Val Asn Pro Val Pro Thr Thr Ala Ser Pro
        50                  55                  60

Ile Ser Ser Ile Phe Ser Arg Ile Gly Asp Pro Ala Leu Asn Met Glu
65                  70                  75                  80

Asn Ile Thr Ser Gly Phe Leu Gly Pro Leu Leu Val Leu Gln Ala Gly
                85                  90                  95

Phe Phe Leu Leu Thr Lys Ile Leu Thr Ile Pro Gln Ser Leu Asp Ser
            100                 105                 110

Trp Trp Thr Ser Leu Asn Phe Leu Gly Gly Thr Thr Val Cys Leu Gly
        115                 120                 125

Gln Asn Ser Gln Ser Pro Thr Ser Asn His Ser Pro Thr Ser Cys Pro
    130                 135                 140

Pro Thr Cys Pro Gly Tyr Arg Trp Met Cys Leu Arg Arg Ser Ile Ile
145                 150                 155                 160

Phe Leu Phe Ile Leu Leu Leu Cys Leu Ile Phe Leu Leu Val Leu Leu
                165                 170                 175

Asp Tyr Gln Gly Met Leu Pro Val Cys Pro Leu Ile Pro Gly Ser Ser
            180                 185                 190

Thr Thr Ser Ala Gly Pro Cys Arg Thr Cys Thr Thr Thr Ala Gln Gly
        195                 200                 205

Thr Ser Met Tyr Pro Ser Cys Cys Cys Thr Lys Pro Ser Asp Gly Asn
    210                 215                 220

Cys Thr Cys Ile Pro Ile Pro Ser Ser Trp Ala Phe Gly Lys Phe Leu
225                 230                 235                 240

Trp Glu Trp Ala Ser Ala Arg Phe Ser Trp Leu Ser Leu Leu Val Pro
                245                 250                 255

Phe Val Gln Trp Phe Val Gly Leu Ser Pro Thr Val Trp Leu Ser Val
            260                 265                 270

Ile Trp Met Met Trp Tyr Trp Gly Pro Ser Leu Phe Ser Xaa Val Lys
        275                 280                 285

```
Pro Phe Leu Pro Leu Leu Pro Ile Phe Xaa Cys Leu Trp Val Xaa Ile
    290                 295                 300
```

<210> SEQ ID NO 21
<211> LENGTH: 938
<212> TYPE: DNA
<213> ORGANISM: Hepatitis B Virus

<400> SEQUENCE: 21

```
ctccaccacg ttccaccaaa ctcttcaaga tcccagagtc agggccctgt acttcctgc     60
tggtggctcc agttcaggaa cagtgagccc tgctcagaat actgtctctg ccatatcgtc    120
aatcttatcg aagactgggg accctgtacc gaacatggag aacatcgcat caggactcct    180
aggaccctg ctcgtgttac aggcggggtt tttctcgttg acaaaaatcc tcacaatacc    240
acagagtcta gactcgtggt ggacttctct caattttcta ggggaaacac ccgtgtgtct    300
tggccaaaat tcgcagtccc aaatctccag tcactcacca acctgttgtc ctccaatttg    360
tcctggttat cgctggatgt gtctgcggcg ttttatcatc ttcctctgca tcctgctgct    420
atgcctcatc ttcttgttgg ttcttctgga ctatcaaggt atgttgcccg tttgtcctct    480
aattccagga tcatcaacga ccagcaccgg accatgcaaa acctgcacaa cgcctgctca    540
aggaacctct atgttwccct catgttgctg tacaaaacct acggacggaa actgcacctg    600
tattcccatc ccatcatctt gggctttcgc aaaataccta tgggagtggg cctcagtccg    660
tttctcatgg ttcagtttac tagtgccatt tgttcagtgg ttcgtagggc tttcccccac    720
tgtctggctt tcagttatat ggatgatgtg gttttggggg ccaagtctgt acaacmtctt    780
gastcccttt atgccgctgt taccaatttt cttctgtctt tgggtataca tttaaaccct    840
gacaaaacaa aaarakgggg atattccctc aacttcatgg gatatgtawt tgggagttgg    900
ggcacattgc cacaggaaca tattgtmcaa aaatcaa                              938
```

<210> SEQ ID NO 22
<211> LENGTH: 312
<212> TYPE: PRT
<213> ORGANISM: Hepatitis B Virus
<220> FEATURE:
<221> NAME/KEY: misc_feature
<222> LOCATION: (186)..(186)
<223> OTHER INFORMATION: Xaa can be Thr or Ser
<220> FEATURE:
<221> NAME/KEY: misc_feature
<222> LOCATION: (259)..(259)
<223> OTHER INFORMATION: Xaa can be His or Pro
<220> FEATURE:
<221> NAME/KEY: misc_feature
<222> LOCATION: (261)..(261)
<223> OTHER INFORMATION: Xaa can be Asp or Glu
<220> FEATURE:
<221> NAME/KEY: misc_feature
<222> LOCATION: (285)..(285)
<223> OTHER INFORMATION: Xaa can be Lys or Arg
<220> FEATURE:
<221> NAME/KEY: misc_feature
<222> LOCATION: (286)..(286)
<223> OTHER INFORMATION: Xaa can be Gly or Trp
<220> FEATURE:
<221> NAME/KEY: misc_feature
<222> LOCATION: (297)..(297)
<223> OTHER INFORMATION: Xaa can be Ile or Phe

<400> SEQUENCE: 22

```
Leu His His Val Pro Pro Asn Ser Ser Arg Ser Gln Ser Gln Gly Pro
1               5                   10                  15

Val Leu Ser Cys Trp Trp Leu Gln Phe Arg Asn Ser Glu Pro Cys Ser
```

```
                20                  25                  30
Glu Tyr Cys Leu Cys His Ile Val Asn Leu Ile Glu Asp Trp Gly Pro
             35                  40                  45

Cys Thr Glu His Gly Glu His Arg Ile Arg Thr Pro Arg Thr Pro Ala
 50                  55                  60

Arg Val Thr Gly Gly Val Phe Leu Val Asp Lys Asn Pro His Asn Thr
 65                  70                  75                  80

Thr Glu Ser Arg Leu Val Val Asp Phe Ser Gln Phe Ser Arg Gly Asn
                 85                  90                  95

Thr Arg Val Ser Trp Pro Lys Phe Ala Val Pro Asn Leu Gln Ser Leu
            100                 105                 110

Thr Asn Leu Leu Ser Ser Asn Leu Ser Trp Leu Ser Leu Asp Val Ser
            115                 120                 125

Ala Ala Phe Tyr His Leu Pro Leu His Pro Ala Ala Met Pro His Leu
        130                 135                 140

Leu Val Gly Ser Ser Gly Leu Ser Arg Tyr Val Ala Arg Leu Ser Ser
145                 150                 155                 160

Asn Ser Arg Ile Ile Asn Asp Gln His Arg Thr Met Gln Asn Leu His
                165                 170                 175

Asn Ala Cys Ser Arg Asn Leu Tyr Val Xaa Leu Met Leu Leu Tyr Lys
            180                 185                 190

Thr Tyr Gly Arg Lys Leu His Leu Tyr Ser His Pro Ile Ile Leu Gly
        195                 200                 205

Phe Arg Lys Ile Pro Met Gly Val Gly Leu Ser Pro Phe Leu Met Val
    210                 215                 220

Gln Phe Thr Ser Ala Ile Cys Ser Val Val Arg Arg Ala Phe Pro His
225                 230                 235                 240

Cys Leu Ala Phe Ser Tyr Met Asp Asp Val Val Leu Gly Ala Lys Ser
                245                 250                 255

Val Gln Xaa Leu Xaa Ser Leu Tyr Ala Ala Val Thr Asn Phe Leu Leu
            260                 265                 270

Ser Leu Gly Ile His Leu Asn Pro Asp Lys Thr Lys Xaa Xaa Gly Tyr
        275                 280                 285

Ser Leu Asn Phe Met Gly Tyr Val Xaa Gly Ser Trp Gly Thr Leu Pro
    290                 295                 300

Gln Glu His Ile Val Gln Lys Ile
305                 310

<210> SEQ ID NO 23
<211> LENGTH: 277
<212> TYPE: PRT
<213> ORGANISM: Hepatitis B Virus
<220> FEATURE:
<221> NAME/KEY: misc_feature
<222> LOCATION: (185)..(185)
<223> OTHER INFORMATION: Xaa can be Leu or Phe
<220> FEATURE:
<221> NAME/KEY: misc_feature
<222> LOCATION: (259)..(259)
<223> OTHER INFORMATION: Xaa can be Ile or Leu
<220> FEATURE:
<221> NAME/KEY: misc_feature
<222> LOCATION: (261)..(261)
<223> OTHER INFORMATION: Xaa can be Thr or Ser

<400> SEQUENCE: 23

Ser Thr Thr Phe His Gln Thr Leu Gln Asp Pro Arg Val Arg Ala Leu
1               5                   10                  15
```

Tyr Phe Pro Ala Gly Gly Ser Ser Gly Thr Val Ser Pro Ala Gln
             20                  25                  30

Asn Thr Val Ser Ala Ile Ser Ser Ile Leu Ser Lys Thr Gly Asp Pro
             35                  40                  45

Val Pro Asn Met Glu Asn Ile Ala Ser Gly Leu Leu Gly Pro Leu Leu
 50                  55                  60

Val Leu Gln Ala Gly Phe Phe Ser Leu Thr Lys Ile Leu Thr Ile Pro
 65                  70                  75                  80

Gln Ser Leu Asp Ser Trp Trp Thr Ser Leu Asn Phe Leu Gly Glu Thr
                 85                  90                  95

Pro Val Cys Leu Gly Gln Asn Ser Gln Ser Gln Ile Ser Ser His Ser
            100                 105                 110

Pro Thr Cys Cys Pro Pro Ile Cys Pro Gly Tyr Arg Trp Met Cys Leu
            115                 120                 125

Arg Arg Phe Ile Ile Phe Leu Cys Ile Leu Leu Leu Cys Leu Ile Phe
130                 135                 140

Leu Leu Val Leu Leu Asp Tyr Gln Gly Met Leu Pro Val Cys Pro Leu
145                 150                 155                 160

Ile Pro Gly Ser Ser Thr Thr Ser Thr Gly Pro Cys Lys Thr Cys Thr
                165                 170                 175

Thr Pro Ala Gln Gly Thr Ser Met Xaa Pro Ser Cys Cys Thr Lys
            180                 185                 190

Pro Thr Asp Gly Asn Cys Thr Cys Ile Pro Ile Pro Ser Ser Trp Ala
            195                 200                 205

Phe Ala Lys Tyr Leu Trp Glu Trp Ala Ser Val Arg Phe Ser Trp Phe
    210                 215                 220

Ser Leu Leu Val Pro Phe Val Gln Trp Phe Val Gly Leu Ser Pro Thr
225                 230                 235                 240

Val Trp Leu Ser Val Ile Trp Met Met Trp Phe Trp Gly Pro Ser Leu
                245                 250                 255

Tyr Asn Xaa Leu Xaa Pro Phe Met Pro Leu Leu Pro Ile Phe Phe Cys
            260                 265                 270

Leu Trp Val Tyr Ile
            275

<210> SEQ ID NO 24
<211> LENGTH: 762
<212> TYPE: DNA
<213> ORGANISM: Hepatitis B Virus

<400> SEQUENCE: 24
cagcgagccc tgctcagaat actgtctctg ccatatcgtc aatcttatcg aagactgggg      60
accctgtacc gaacatggag aacatcgcat caggactcct aggaccctg ctcgtgttac     120
aggcggggtt tttcttgttg acaaaaatcc tcacaatacc acagagtcta gactcgtggt     180
ggacttctct caatttctta ggggggacac cgtgtgtct tggccaaaat cgcagtccc      240
aaatctccag tcactcacca acttgttgtc ctccaacttg tcctggttat cgctggatgt     300
atctgcggcg ttttatcatc ttcctctgca tcctgctgct atgcctcatc ttcttgttgg     360
ttcttctgga ctatcaaggt atgttgcccg tatgtcctct aattccagga tcatcaacaa     420
ccagcaccgg accatgcaaa acctgcacga ctcctgctca aggaacctct atgtttccct     480
catgttgctg tacaaaacct acggacggaa actgcacctg tattcccatc ccatcatctt     540
gggctttcgc aaaataccta tgggagtggg cctcagtccg tttctcttgg ytcagtttac     600

```
tagtgccatt tgttcagtgg ttcgtagggc tttcccccac tgtctggctt tcagttatat    660
ggatgatgtg ttttgggggg ccaagtctgc acaacatctt gagtcccttty atgccgctgt    720 taccaattt  cttttgtctt tgggtataca tttaaccct  ca                        762
```

```
<210> SEQ ID NO 25
<211> LENGTH: 253
<212> TYPE: PRT
<213> ORGANISM: Hepatitis B Virus
<220> FEATURE:
<221> NAME/KEY: misc_feature
<222> LOCATION: (197)..(197)
<223> OTHER INFORMATION: Xaa can be Ala or Val
<220> FEATURE:
<221> NAME/KEY: misc_feature
<222> LOCATION: (237)..(237)
<223> OTHER INFORMATION: Xaa can be His or Tyr

<400> SEQUENCE: 25
```

```
Ser Glu Pro Cys Ser Glu Tyr Cys Leu Cys His Ile Val Asn Leu Ile
1               5                   10                  15

Glu Asp Trp Gly Pro Cys Thr Glu His Gly Glu His Arg Ile Arg Thr
            20                  25                  30

Pro Arg Thr Pro Ala Arg Val Thr Gly Gly Val Phe Leu Val Asp Lys
        35                  40                  45

Asn Pro His Asn Thr Thr Glu Ser Arg Leu Val Val Asp Phe Ser Gln
    50                  55                  60

Phe Ser Arg Gly Asp Thr Arg Val Ser Trp Pro Lys Phe Ala Val Pro
65                  70                  75                  80

Asn Leu Gln Ser Leu Thr Asn Leu Leu Ser Ser Asn Leu Ser Trp Leu
                85                  90                  95

Ser Leu Asp Val Ser Ala Ala Phe Tyr His Leu Pro Leu His Pro Ala
            100                 105                 110

Ala Met Pro His Leu Leu Val Gly Ser Ser Gly Leu Ser Arg Tyr Val
        115                 120                 125

Ala Arg Met Ser Ser Asn Ser Arg Ile Ile Asn Asn Gln His Arg Thr
    130                 135                 140

Met Gln Asn Leu His Asp Ser Cys Ser Arg Asn Leu Tyr Val Ser Leu
145                 150                 155                 160

Met Leu Leu Tyr Lys Thr Tyr Gly Arg Lys Leu His Leu Tyr Ser His
                165                 170                 175

Pro Ile Ile Leu Gly Phe Arg Lys Ile Pro Met Gly Val Gly Leu Ser
            180                 185                 190

Pro Phe Leu Leu Xaa Gln Phe Thr Ser Ala Ile Cys Ser Val Val Arg
        195                 200                 205

Arg Ala Phe Pro His Cys Leu Ala Phe Ser Tyr Met Asp Asp Val Val
    210                 215                 220

Leu Gly Ala Lys Ser Ala Gln His Leu Glu Ser Leu Xaa Ala Ala Val
225                 230                 235                 240

Thr Asn Phe Leu Leu Ser Leu Gly Ile His Leu Thr Pro
                245                 250
```

```
<210> SEQ ID NO 26
<211> LENGTH: 250
<212> TYPE: PRT
<213> ORGANISM: Hepatitis B Virus
<220> FEATURE:
<221> NAME/KEY: misc_feature
<222> LOCATION: (197)..(197)
<223> OTHER INFORMATION: Xaa can be Leu or Phe
```

<400> SEQUENCE: 26

Ala Ser Pro Ala Gln Asn Thr Val Ser Ala Ile Ser Ser Ile Leu Ser
1               5                   10                  15

Lys Thr Gly Asp Pro Val Pro Asn Met Glu Asn Ile Ala Ser Gly Leu
            20                  25                  30

Leu Gly Pro Leu Leu Val Leu Gln Ala Gly Phe Phe Leu Leu Thr Lys
        35                  40                  45

Ile Leu Thr Ile Pro Gln Ser Leu Asp Ser Trp Trp Thr Ser Leu Asn
50                  55                  60

Phe Leu Gly Gly Thr Pro Val Cys Leu Gly Gln Asn Ser Gln Ser Gln
65                  70                  75                  80

Ile Ser Ser His Ser Pro Thr Cys Cys Pro Pro Thr Cys Pro Gly Tyr
                85                  90                  95

Arg Trp Met Tyr Leu Arg Arg Phe Ile Ile Phe Leu Cys Ile Leu Leu
            100                 105                 110

Leu Cys Leu Ile Phe Leu Leu Val Leu Leu Asp Tyr Gln Gly Met Leu
        115                 120                 125

Pro Val Cys Pro Leu Ile Pro Gly Ser Ser Thr Thr Ser Thr Gly Pro
130                 135                 140

Cys Lys Thr Cys Thr Thr Pro Ala Gln Gly Thr Ser Met Phe Pro Ser
145                 150                 155                 160

Cys Cys Cys Thr Lys Pro Thr Asp Gly Asn Cys Thr Cys Ile Pro Ile
                165                 170                 175

Pro Ser Ser Trp Ala Phe Ala Lys Tyr Leu Trp Glu Trp Ala Ser Val
            180                 185                 190

Arg Phe Ser Trp Xaa Ser Leu Leu Val Pro Phe Val Gln Trp Phe Val
        195                 200                 205

Gly Leu Ser Pro Thr Val Trp Leu Ser Val Ile Trp Met Met Trp Phe
210                 215                 220

Trp Gly Pro Ser Leu His Asn Ile Leu Ser Pro Phe Met Pro Leu Leu
225                 230                 235                 240

Pro Ile Phe Phe Cys Leu Trp Val Tyr Ile
                245                 250

<210> SEQ ID NO 27
<211> LENGTH: 818
<212> TYPE: DNA
<213> ORGANISM: Hepatitis B Virus

<400> SEQUENCE: 27
gaggattggg gaccctgcgc tgaatatgga gaacatcaca tcaggattcc taggacccct        60
tctcgtgtta caggcggggt ttttcttgtt gacaagaatc ctcacaatac cgcagagtct       120
agastcgtgg tggacttctc tcaatttcct aggggsaacc accgtgtgtc ttggccaaaa       180
ttcgcagtcc ccaacctcca atcactacc aacctcctgt cctccgactt gacctggtta       240
tcgctggatg tgactgcggc attttatcat attcctcttc atcctgctgc tatgcctcat       300
cttcttgttg gttcttctgg actatcaagg tatgttgccc gtttgtcctc taattccagg       360
atcctcaacc accagcacgg gaacatgccg aacttgcacg actcctgctc aaggaacctc       420
tatgtatccc tcctgttgct gtaccaaacc ttcggacgga aattgcacct gtattcccat       480
cccatcatcc tgggctttcg gaaaattcct atgggagtgg gcctcagccc gtttctcatg       540
gctcagtttg gtagtgccat tgttcagtg gttcgtaggg ctttccccca ctgtttggct       600

```
ttcatttatg tggatgatrt ggtattgggg gccaagtctg tacagcatct tgagtccctt    660
tttaccgctg ttaccaattt tcttttgtct ctgggtatac atttgrwccc tmacaaaaca    720
aagagatggg gttactccct aaattttatg ggctatgtca ttggatgtta tgggtccttg    780
ccacaagaac acatcataca taaaatcaaa gaatgttt                            818
```

<210> SEQ ID NO 28
<211> LENGTH: 272
<212> TYPE: PRT
<213> ORGANISM: Hepatitis B Virus
<220> FEATURE:
<221> NAME/KEY: misc_feature
<222> LOCATION: (42)..(42)
<223> OTHER INFORMATION: Xaa can be Leu or Val
<220> FEATURE:
<221> NAME/KEY: misc_feature
<222> LOCATION: (207)..(207)
<223> OTHER INFORMATION: Xaa can be Met or Val
<220> FEATURE:
<221> NAME/KEY: misc_feature
<222> LOCATION: (236)..(236)
<223> OTHER INFORMATION: Xaa can be Asn, Ile, Asp or Val
<220> FEATURE:
<221> NAME/KEY: misc_feature
<222> LOCATION: (238)..(238)
<223> OTHER INFORMATION: Xaa can be Asn or His

<400> SEQUENCE: 28

```
Glu Asp Trp Gly Pro Cys Ala Glu Tyr Gly Glu His His Ile Arg Ile
1               5                   10                  15

Pro Arg Thr Pro Ser Arg Val Thr Gly Gly Val Phe Leu Val Asp Lys
            20                  25                  30

Asn Pro His Asn Thr Ala Glu Ser Arg Xaa Val Val Asp Phe Ser Gln
        35                  40                  45

Phe Ser Arg Gly Asn His Arg Val Ser Trp Pro Lys Phe Ala Val Pro
    50                  55                  60

Asn Leu Gln Ser Leu Thr Asn Leu Leu Ser Ser Asp Leu Thr Trp Leu
65                  70                  75                  80

Ser Leu Asp Val Thr Ala Ala Phe Tyr His Ile Pro Leu His Pro Ala
                85                  90                  95

Ala Met Pro His Leu Leu Val Gly Ser Ser Gly Leu Ser Arg Tyr Val
            100                 105                 110

Ala Arg Leu Ser Ser Asn Ser Arg Ile Leu Asn His Gln His Gly Asn
        115                 120                 125

Met Pro Asn Leu His Asp Ser Cys Ser Arg Asn Leu Tyr Val Ser Leu
    130                 135                 140

Leu Leu Leu Tyr Gln Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Met Ala Gln Phe Gly Ser Ala Ile Cys Ser Val Val Arg
            180                 185                 190

Arg Ala Phe Pro His Cys Leu Ala Phe Ile Tyr Val Asp Asp Xaa Val
        195                 200                 205

Leu Gly Ala Lys Ser Val Gln His Leu Glu Ser Leu Phe Thr Ala Val
    210                 215                 220

Thr Asn Phe Leu Leu Ser Leu Gly Ile His Leu Xaa Pro Xaa Lys Thr
225                 230                 235                 240

Lys Arg Trp Gly Tyr Ser Leu Asn Phe Met Gly Tyr Val Ile Gly Cys
                245                 250                 255
```

```
Tyr Gly Ser Leu Pro Gln Glu His Ile Ile His Lys Ile Lys Glu Cys
            260                 265                 270

<210> SEQ ID NO 29
<211> LENGTH: 225
<212> TYPE: PRT
<213> ORGANISM: Hepatitis B Virus
<220> FEATURE:
<221> NAME/KEY: misc_feature
<222> LOCATION: (33)..(33)
<223> OTHER INFORMATION: Xaa can be Asp or Glu
<220> FEATURE:
<221> NAME/KEY: misc_feature
<222> LOCATION: (44)..(44)
<223> OTHER INFORMATION: Xaa can be Ala or Gly
<220> FEATURE:
<221> NAME/KEY: misc_feature
<222> LOCATION: (196)..(196)
<223> OTHER INFORMATION: Xaa can be Ile or Met

<400> SEQUENCE: 29

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Xaa Ser Trp Trp Thr Ser Leu Asn Phe Leu Gly Xaa Thr Thr Val Cys
        35                  40                  45

Leu Gly Gln Asn Ser Gln Ser Pro Thr Ser Asn His Ser Pro Thr Ser
50                  55                  60

Cys Pro Pro Thr Pro Gly Tyr Arg Trp Met Leu Arg His Phe Ile Ile
65                  70                  75                  80

Phe Leu Phe Ile Leu Leu Leu Cys Leu Ile Phe Leu Leu Val Leu Leu
                85                  90                  95

Asp Tyr Gln Gly Met Leu Pro Val Cys Pro Leu Ile Pro Gly Ser Ser
            100                 105                 110

Thr Thr Ser Thr Gly Thr Cys Arg Thr Cys Thr Thr Pro Ala Gln Gly
        115                 120                 125

Thr Ser Met Tyr Pro Ser Cys Cys Cys Thr Lys Pro Ser Asp Gly Asn
130                 135                 140

Cys Thr Cys Ile Pro Ile Pro Ser Ser Trp Ala Phe Gly Lys Phe Leu
145                 150                 155                 160

Trp Glu Trp Ala Ser Ala Arg Phe Ser Trp Leu Ser Leu Val Val Pro
                165                 170                 175

Phe Val Gln Trp Phe Val Gly Leu Ser Pro Thr Val Trp Leu Ser Phe
            180                 185                 190

Met Trp Met Xaa Trp Tyr Trp Gly Pro Ser Leu Tyr Ser Ile Leu Ser
        195                 200                 205

Pro Phe Leu Pro Leu Leu Pro Ile Phe Phe Cys Leu Trp Val Tyr Ile
210                 215                 220

Trp
225

<210> SEQ ID NO 30
<211> LENGTH: 683
<212> TYPE: DNA
<213> ORGANISM: Hepatitis B Virus

<400> SEQUENCE: 30
atcgcagtcc ccaacctcca atcactcacc aacctcctgt cctccaactt gacctggtta        60
```

```
tcgctggatr tgtctgcggc gttttatcat cttcctcttc atcctgctgc tatgcctcat    120
cttcttgttg gttcttctgg actatcaagg tatgttgccc gtttgtcctc taattccagg    180
atcmtcaacc accagcacgg gaccatgcag racctgcacg actcctgctc aaggaacctc    240
tatgaatccc tcctgttgct gtwccraacc ttcggacgga aattgcacct gtattcccat    300
cccatcatcc tgggctttcg gaaaattcct atgggagtgg gcctcagccc gtttctcctg    360
gctcarttta ctagtgcyat tgttcagtg gttcgtaggg cttccccca ctgtktggct     420 ttcagttata trgatgatgt ggtattgggg gccaagtctg tacagcatct tgagkcccctt  480 twtaccgctg ttaccaattt tcttttgtct ctgggtayac atttaaaccc tcacaaaaca   540
aaaagatggg gttacymttt acatttcatg ggctatgtca ttggatgtta tgggtcattg   600
ccacaagatc acatcakaca gaaaatcaaa gaatgtttta gaaaacttcc tgttaatagg   660
cctattgatt ggaaagtatg tca                                           683
```

<210> SEQ ID NO 31
<211> LENGTH: 227
<212> TYPE: PRT
<213> ORGANISM: Hepatitis B Virus
<220> FEATURE:
<221> NAME/KEY: misc_feature
<222> LOCATION: (24)..(24)
<223> OTHER INFORMATION: Xaa can be Met or Val
<220> FEATURE:
<221> NAME/KEY: misc_feature
<222> LOCATION: (62)..(62)
<223> OTHER INFORMATION: Xaa can be Ile or Leu
<220> FEATURE:
<221> NAME/KEY: misc_feature
<222> LOCATION: (71)..(71)
<223> OTHER INFORMATION: Xaa can be Asn or Asp
<220> FEATURE:
<221> NAME/KEY: misc_feature
<222> LOCATION: (88)..(88)
<223> OTHER INFORMATION: Xaa can be Tyr or Phe
<220> FEATURE:
<221> NAME/KEY: misc_feature
<222> LOCATION: (89)..(89)
<223> OTHER INFORMATION: Xaa can be Gln or Phe
<220> FEATURE:
<221> NAME/KEY: misc_feature
<222> LOCATION: (139)..(139)
<223> OTHER INFORMATION: Xaa can be Val or Leu
<220> FEATURE:
<221> NAME/KEY: misc_feature
<222> LOCATION: (144)..(144)
<223> OTHER INFORMATION: Xaa can be Ile or Met
<220> FEATURE:
<221> NAME/KEY: misc_feature
<222> LOCATION: (159)..(159)
<223> OTHER INFORMATION: Xaa can be Ala or Ser
<220> FEATURE:
<221> NAME/KEY: misc_feature
<222> LOCATION: (161)..(161)
<223> OTHER INFORMATION: Xaa can be Tyr or Phe
<220> FEATURE:
<221> NAME/KEY: misc_feature
<222> LOCATION: (173)..(173)
<223> OTHER INFORMATION: Xaa can be Thr or Ile
<220> FEATURE:
<221> NAME/KEY: misc_feature
<222> LOCATION: (186)..(186)
<223> OTHER INFORMATION: Xaa can be His, Pro, Tyr or Ser
<220> FEATURE:
<221> NAME/KEY: misc_feature
<222> LOCATION: (206)..(206)
<223> OTHER INFORMATION: Xaa can be Arg or Ile

<400> SEQUENCE: 31

Ile Ala Val Pro Asn Leu Gln Ser Leu Thr Asn Leu Leu Ser Ser Asn

```
                1               5                  10                 15
Leu Thr Trp Leu Ser Leu Asp Xaa Ser Ala Ala Phe Tyr His Leu Pro
                20                 25                 30

Leu His Pro Ala Ala Met Pro His Leu Leu Val Gly Ser Ser Gly Leu
                35                 40                 45

Ser Arg Tyr Val Ala Arg Leu Ser Ser Asn Ser Arg Ile Xaa Asn His
            50                 55                 60

Gln His Gly Thr Met Gln Xaa Leu His Asp Ser Cys Ser Arg Asn Leu
65                 70                 75                 80

Tyr Glu Ser Leu Leu Leu Xaa Xaa Thr Phe Gly Arg Lys Leu His
                85                 90                 95

Leu Tyr Ser His Pro Ile Ile Leu Gly Phe Arg Lys Ile Pro Met Gly
                100                105                110

Val Gly Leu Ser Pro Phe Leu Leu Ala Gln Phe Thr Ser Ala Ile Cys
                115                120                125

Ser Val Val Arg Arg Ala Phe Pro His Cys Xaa Ala Phe Ser Tyr Xaa
            130                135                140

Asp Asp Val Val Leu Gly Ala Lys Ser Val Gln His Leu Glu Xaa Leu
145                150                155                160

Xaa Thr Ala Val Thr Asn Phe Leu Leu Ser Leu Gly Xaa His Leu Asn
                165                170                175

Pro His Lys Thr Lys Arg Trp Gly Tyr Xaa Leu His Phe Met Gly Tyr
                180                185                190

Val Ile Gly Cys Tyr Gly Ser Leu Pro Gln Asp His Ile Xaa Gln Lys
                195                200                205

Ile Lys Glu Cys Phe Arg Lys Leu Pro Val Asn Arg Pro Ile Asp Trp
                210                215                220

Lys Val Cys
225

<210> SEQ ID NO 32
<211> LENGTH: 173
<212> TYPE: PRT
<213> ORGANISM: Hepatitis B Virus
<220> FEATURE:
<221> NAME/KEY: misc_feature
<222> LOCATION: (22)..(22)
<223> OTHER INFORMATION: Xaa can be Ile or Met
<220> FEATURE:
<221> NAME/KEY: misc_feature
<222> LOCATION: (87)..(87)
<223> OTHER INFORMATION: Xaa can be Thr or Ser
<220> FEATURE:
<221> NAME/KEY: misc_feature
<222> LOCATION: (88)..(88)
<223> OTHER INFORMATION: Xaa can be Lys or Glu
<220> FEATURE:
<221> NAME/KEY: misc_feature
<222> LOCATION: (121)..(121)
<223> OTHER INFORMATION: Xaa can be Asn or Ser
<220> FEATURE:
<221> NAME/KEY: misc_feature
<222> LOCATION: (125)..(125)
<223> OTHER INFORMATION: Xaa can be Pro or Leu
<220> FEATURE:
<221> NAME/KEY: misc_feature
<222> LOCATION: (157)..(157)
<223> OTHER INFORMATION: Xaa can be Arg or Ser
<220> FEATURE:
<221> NAME/KEY: misc_feature
<222> LOCATION: (160)..(160)
<223> OTHER INFORMATION: Xaa can be Ile or Leu
<220> FEATURE:
<221> NAME/KEY: misc_feature
```

```
<222> LOCATION: (172)..(172)
<223> OTHER INFORMATION: Xaa can be His or Tyr

<400> SEQUENCE: 32

Ser Gln Ser Pro Thr Ser Asn His Ser Pro Thr Ser Cys Pro Pro Thr
1               5                   10                  15

Pro Gly Tyr Arg Trp Xaa Cys Leu Arg Arg Phe Ile Ile Phe Leu Phe
            20                  25                  30

Ile Leu Leu Leu Cys Leu Ile Phe Leu Leu Val Leu Leu Asp Tyr Gln
            35                  40                  45

Gly Met Leu Pro Val Cys Pro Leu Ile Pro Gly Ser Ser Thr Thr Ser
        50                  55                  60

Thr Gly Pro Cys Arg Thr Cys Thr Thr Pro Ala Gln Gly Thr Ser Met
65                  70                  75                  80

Asn Pro Ser Cys Cys Cys Xaa Xaa Pro Ser Asp Gly Asn Cys Thr Cys
            85                  90                  95

Ile Pro Ile Pro Ser Ser Trp Ala Phe Gly Lys Phe Leu Trp Glu Trp
            100                 105                 110

Ala Ser Ala Arg Phe Ser Trp Leu Xaa Leu Leu Val Xaa Phe Val Gln
            115                 120                 125

Trp Phe Val Gly Leu Ser Pro Thr Val Trp Leu Ser Val Ile Trp Met
        130                 135                 140

Met Trp Tyr Trp Gly Pro Ser Leu Tyr Ser Ile Leu Xaa Pro Phe Xaa
145                 150                 155                 160

Pro Leu Leu Pro Ile Phe Phe Cys Leu Trp Val Xaa Ile
                165                 170
```